といった | United States Patent [19] | [11] 4,325,962
Rainer | [45] Apr. 20, 1982

[54] PHARMACEUTICAL COMPOSITIONS COMPRISING A PYRAZOLE DERIVATIVE AND METHOD OF USE

[75] Inventor: Georg Rainer, Konstanz, Fed. Rep. of Germany

[73] Assignee: Byk-Gulden Lomberg Chemische Fabrik GmbH, Fed. Rep. of Germany

[21] Appl. No.: 969,872

[22] Filed: Dec. 15, 1978

Related U.S. Application Data

[62] Division of Ser. No. 72,233, Sep. 14, 1970, Pat. No. 4,146,721.

[30] Foreign Application Priority Data

Sep. 12, 1969 [DE] Fed. Rep. of Germany ....... 1946370

[51] Int. Cl.³ .......................................... A61K 31/415
[52] U.S. Cl. .................................. 424/273 P; 424/180
[58] Field of Search .............................. 548/374, 378; 424/273 P, 180

[56] References Cited

U.S. PATENT DOCUMENTS

| 3,704,241 | 11/1972 | Noguchi et al. | 424/273 P |
| 4,042,702 | 8/1977 | Rainer | 548/374 |
| 4,095,025 | 6/1978 | Newberry | 424/273 P |
| 4,146,721 | 3/1979 | Rainer | 548/378 |

FOREIGN PATENT DOCUMENTS

| 1946370 | 4/1971 | Fed. Rep. of Germany | 548/378 |
| 2605243 | 9/1976 | Fed. Rep. of Germany | 424/273 P |
| 2133503 | 12/1972 | France | 424/273 P |

*Primary Examiner*—Henry R. Jiles
*Assistant Examiner*—Natalia Harkaway
*Attorney, Agent, or Firm*—Weiser, Stapler & Spivak

[57] ABSTRACT

Pyrazol-4-acetic acid compounds, such as substituted pyrazol-4-acetic acid, its esters, amides, nitriles and their pharmaceutically acceptable salts and method for the preparation of these compounds are disclosed. The novel compounds are useful analgesics, anti-inflammatory, and antipyretics.

41 Claims, No Drawings

PHARMACEUTICAL COMPOSITIONS COMPRISING A PYRAZOLE DERIVATIVE AND METHOD OF USE

The present application is a divisional of U.S. Ser. No. 72,233, filed Sept. 14, 1970 now U.S. Pat. No. 4,146,721 issued Mar. 27, 1979.

This invention relates to new substituted pyrazol compounds hving excellent antiphlogistic (antiinflammatory), analgesic and antipyretic properties.

It is known, that 2-methyl-5-methoxy-1-(p-chlorobenzoyl)-indol-3-acetic acid described in Belgian Pat. No. 615,395, and known as "Indomethacin" shows antiphlogistic, analgesic and antipyretic effects, surpassing in this respect the effectiveness of the well known 4-n-butyl-1,2-diphenyl-3,5-dioxopyrazolidine. (J. Am. Chem. So. 85, 488 (1963). However, as is well known, Indomethacin produces many undesirable side effects. Chem. Eng. News, 46 (1968).

The new pyrazol-4-acetic acid derivatives of the invention and their pharmacologically acceptable salts with inorganic or organic bases correspond to the general Formula I

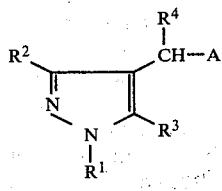

where $R^1$, $R^2$ and $R^3$ are identical or different, and wherein each of these substituents represents hydrogen, a linear or branched, saturated or unsaturated aliphatic or cycloaliphatic hydrocarbon radical having from 1 to 7 carbon atoms or an unsubstituted or substituted aryl or heteroaryl group having up to 12 carbon atoms, and $R^1$ may also represent a benzyl radical, a benzyl substituted by one halogen or one alkoxy group having from 1 to 4 carbon atoms;

$R^4$ represents hydrogen or alkyl having from 1 to 3 carbon atoms or cycloalkyl having from 3 to 6 carbon atoms;

A represents the $-COOH$, $-COOR^5$, $-CONR^6R^7$, $-CN$ or $-C(=NOH)OH$ radicals, wherein $R^5$ represents alkyl having from 1 to 4 carbon atoms, benzyl, phenyl or 2-carboxyphenyl, and wherein $R^6$ and $R^7$ each represents hydrogen and/or alkyl having from 1 to 4 carbon atoms, or $R^6$ and $R^7$, together with the nitrogen atom of the $-CONR^6R^7$ radical represent a pyrrolidino, a piperidino or a morpholino radical, with the proviso that when $R^2$ is hydrogen, $R^3$ is not hydrogen or methyl.

The preferred group of the pyrazol-4-acetic acid compounds of the invention and of the pharmacologically acceptable salts thereof, comprises those compounds, wherein in the general Formula I A has the significance set out hereinbefore;

$R^1$, $R^2$ and $R^3$ are identical or different, and wherein each of these substituents represents hydrogen, a linear or branched alkyl having from 1 to 7 carbon atoms, cyclopentyl or cyclohexyl, naphthyl, furyl, thienyl, pyridyl, phenyl or substituted phenyl of the formula $-(C_6H_3)R^8R^9$, wherein $R^8$ is hydrogen and $R^9$ is halogen, alkyl, alkoxy, or alkylmercapto each having from 1 to 4 carbon atoms, trifluoromethyl, cyclohexyl or phenyl or each of $R^8$ and $R^9$ is methyl and/or chlorine and/or methoxy, or $R^8$ and $R^9$ together represent trimethylene, tetramethylene or a methylenedioxy grouping, and wherein $R^1$ may also represent halogen substituted benzyl, methoxybenzyl or alkenyl having from 3 to 7 carbon atoms; and wherein $R^4$ represents hydrogen or methyl, with the proviso that if $R^2$ is hydrogen, $R^3$ cannot be hydrogen or methyl A still more preferred group of the pyrazol-4-acetic acid compounds of the invention and of the pharmacologically acceptable salts thereof, comprises those compounds, wherein in the general Formula I A has the significance set out hereinbefore and especially those, wherein A represents the carboxylic group;

$R^1$ represents hydrogen, methyl, ethyl, n-propyl, iso-propyl, n-butyl, iso-butyl, iso-pentyl, allyl, cyclopentyl, cyclohexyl, benzyl, p-chlorobenzyl, phenyl, p-chlorophenyl, m-chlorophenyl, o-chlorophenyl, p-bromophenyl, m-bromophenyl, p-fluorophenyl, p-tolyl, m-tolyl, 3,4-dichlorophenyl, 2,4-dichlorophenyl, 3-chloro-2-methylphenyl, 3,4-dimethylphenyl, α,α,α-trifluoro-m-tolyl, p-methoxyphenyl, p-ethoxyphenyl, 3,4-dimethoxyphenyl, p-biphenylyl, naphthyl or pyridyl;

$R^2$ represents hydrogen, methyl, ethyl, n-propyl, iso-propyl, n-butyl, iso-butyl, tert.-butyl, cyclohexyl, phenyl, p-chlorophenyl, m-chlorophenyl, p-bromophenyl, m-bromophenyl, p-fluorophenyl, p-methoxyphenyl, m-methoxyphenyl, p-ethoxyphenyl, p-propoxyphenyl, p-butoxyphenyl, 3,4-dimethoxyphenyl, 3,4-methylenedioxyphenyl, p-methylmercaptophenyl, p-tolyl, m-tolyl, 3,4-dimethylphenyl, α,α,α-trifluoro-m-tolyl, p-cyclohexylphenyl, 5-indanyl, 6-tetralyl, p-biphenylyl, naphthyl, furyl, thienyl or pyridyl;

$R^3$ represents hydrogen, methyl, ethyl, n-propyl, iso-propyl, iso-butyl, phenyl, p-chlorophenyl, p-bromophenyl, p-methoxyphenyl, m-methoxyphenyl, p-tolyl, furyl or thienyl; and wherein $R^4$ is hydrogen, with the same proviso that if $R^2$ is hydrogen, $R^3$ is not hydrogen or methyl.

The most preferred group of the pyrazol-4-acetic acid compounds of the invention and of the pharmacologically acceptable salts thereof, comprises those compounds, wherein in the general Formula I A is the carboxylic group;

$R^1$ represents phenyl or pyridyl;

$R^2$ represents phenyl, p-halogenophenyl, p-methylphenyl or furyl;

$R^3$ represents hydrogen, phenyl or furyl; and $R^4$ represents hydrogen.

Among the new compounds of the invention, those being of greatest interest at this time are the following compounds:

1-phenyl-3-(p-chlorophenyl)-pyrazol-4-acetic acid
1,3,5-triphenyl-pyrazol-4-acetic acid
1-phenyl-3,5-di-(2-furyl)-pyrazol-4-acetic acid
3,5-diphenyl-1-(3-pyridyl)-pyrazol-4-acetic acid
1-phenyl-3-(p-fluorophenyl)-pyrazol-4-acetic acid
1-phenyl-3-(p-bromophenyl)-pyrazol-4-acetic acid, and
1-phenyl-3-(2-naphthyl)-pyrazol-4-acetic acid.

The present invention concerns furthermore a new method for the production of the new pyrazol-4-acetic acid compounds of the general Formula I set out hereinbefore and of their pharmacologically acceptable salts with inorganic or organic bases.

The new method of the invention comprises the following embodiments:

(a) The carboxylic acids of the general Formula I, wherein A represents —COOH, and $R^1$, $R^2$, $R^3$ and $R^4$ have the significance set out hereinbefore may advantageously be produced;

(1) By the hydrolysis of the esters, thioesters, amides, thioamides, hydrazides, azides, imide acid esters, amidines, nitriles or hydroxamic acids of the desired carboxylic acid.

(2) By the thermolysis of the tert.-alkylesters, preferably the tert.-butylester of the desired carboxylic acid.

(3) By the hydrogenolysis of the benzylester of the desired carboxylic acid.

In embodiments (a) 1-3 of the method, the free acid may be recovered, when desired, by acidification of the solution of the salt. If the salt of the acid is desired, the salt may be recovered, when desired, by evaporation of the solvent or by salting out from the alkaline solution of the salt.

(b) The carboxylic acids, esters and amides of the general Formula I, wherein A represents —COOH, —COOR$^5$ or —CONR$^6$R$^7$, $R^1$, $R^2$, $R^3$ and $R^4$ have the significance set out hereinbefore in connection with general Formula I, and wherein $R^5$ represents alkyl having from 1 to 4 carbon atoms, benzyl or phenyl, and wherein $R^6$ and $R^7$ each represent alkyl having from 1 to 4 carbon atoms or wherein $R^6$ and $R^7$ together with the nitrogen atom of the —CONR$^6$R$^7$-group represent a pyrrolidino, piperidino or morpholino group may advantageously be produced by the reaction of a β-dicarbonyl compound corresponding to the general Formula II or of the corresponding enol derivatives corresponding to the general Formula III with a hydrazine corresponding to the general Formula IV or with the corresponding salt of the hydrazine,

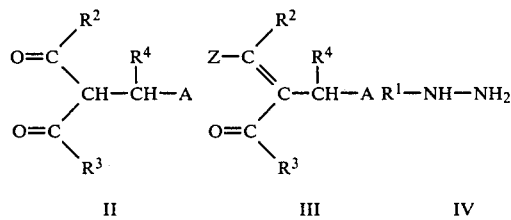

II  III  IV whereby in the general Formulae II, III and IV the substituents $R^1$, $R^2$, $R^3$ and $R^4$ have the significance set out hereinbefore in connection with the general Formula I, A has the significance set out hereinbefore in connection with embodiment (b) of the method, and Z represents —OH, —O alkyl, —O(C=O)alkyl, —NH$_2$ or —N(alkyl)$_2$ wherein the alkyl groups in the listed groups have from 1 to 4 carbon atoms.

(c) The nitriles of the general Formula I, wherein A represents —CN, and $R^1$, $R^2$, $R^3$ and $R^4$ have the significance set out hereinbefore in connection with the general Formula I may advantageously be produced:

(1) By the reaction of the compounds of the general Formula I, wherein A is a halogen atom, preferably chlorine or bromine, and wherein $R^1$, $R^2$, $R^3$ and $R^4$ have the significance set out hereinbefore in connection with the general Formula I, with an alkali metal cyanide or with an alkaline earth metal cyanide, preferably with sodium cyanide or potassium cyanide; or (2) By the reaction of the compounds of the general Formula I, wherein A is —CONH$_2$ and $R^1$, $R^2$, $R^3$ and $R^4$ have the significance set out hereinbefore in connection with the general Formula I, with a dehydration agent, preferably with POCl$_3$, P$_2$O$_5$, PCl$_5$ or SOCl$_2$:

(d) The esters of the general Formula I, wherein A is —COOR$^5$ and wherein $R^1$, $R^2$, $R^3$, $R^4$ and $R^5$ have the significance set out hereinbefore in connection with the general Formula I may advantageously be produced:

(1) By the reaction of the corresponding carboxylic acid, wherein A is —COOH, with a compound having the formula R$^5$OH;

(2) By the reaction of the corresponding carboxylic acid halogenide, wherein A is —COHal, Hal being a halogen atom and preferably a chlorine or bromine atom, with a compound having the formula R$^5$OH; or (3) By the reaction of the corresponding carboxylic anhydride with a compound having the formula R$^5$OH, whereby in the embodiments (d) (1) to (3), $R^5$ in the compound R$^5$OH has the significance set out hereinbefore in connection with the general Formula I;

(e) The amides of the general Formula I, wherein A represents —CONH$_2$ and $R^1$, $R^2$, $R^3$ and $R^4$ have the significance set out hereinbefore in connection with the general Formula I, may advantageously be produced by the hydrolysis of the corresponding nitriles of the general Formula I, wherein A is —CN;

(f) The amides of the general Formula I, wherein A represents —CONR$^6$R$^7$ and wherein $R^1$, $R^2$, $R^3$, $R^4$, $R^6$ and $R^7$ have the significance set out hereinbefore in connection with the general Formula I, may advantageously be produced by the reaction of the corresponding acid chloride, acid bromide, acid anhydride or ester of the general Formula I with an amine of the formula HNR$^6$R$^7$, wherein $R^6$ and $R^7$ have the significance set out hereinbefore in connection with the general Formula I;

(g) The esters of the general Formula I, wherein A is —COOalkyl, the alkyl having from 1 to 4 carbon atoms, and wherein $R^1$, $R^2$, $R^3$ and $R^4$ have the significance set out hereinbefore in connection with the general Formula I, may advantageously be produced by the alcoholysis of the corresponding nitriles of the general Formula I, wherein A is —CN, in the presence of a strong acid, preferably in the presence of hydrochloric acid or sulfuric acid;

(h) The hydroxamic acids of the general Formula I, wherein A is —C(=NOH)OH and wherein $R^1$, $R^2$, $R^3$ and $R^4$ have the significance set out hereinbefore in connection with the general Formula I, may advantageously be produced by the reaction of the corresponding carboxylic acid halogenides of the general Formula I, wherein A is —COHal, Hal being a halogen atom and preferably a chlorine atom or a bromine atom, with hydroxylamine;

(i) The carboxylic acids of the general Formula I, wherein A is —COOH, and wherein $R^1$, $R^2$, $R^3$ and $R^4$ have the significance set out hereinbefore in connection with the general Formula I, are advantageously produced by the reaction of the corresponding compounds of the general Formula I, wherein A represents MeHaL, Me being therein a zinc or cadmium atom and preferably a magnesium atom, and Hal being a halogen atom, preferably a chlorine atom or a bromine atom, with carbon dioxide;

(j) The esters, amides and nitriles of the general Formula I, wherein A is —COOR$^5$, —CONR$^6$R$^7$ or —CN, respectively, and wherein $R^2$, $R^3$ and $R^4$ have the significance set out hereinbefore in connection with the general Formula I, $R^5$ represents alkyl having from 1 to 4 carbon atoms, benzyl or phenyl, and wherein $R^6$ and $R^7$ each represent alkyl having from 1 to 4 carbon atoms or $R^6$ and $R^7$ together with the nitrogen atom of the —$CONR^6R^7$ group represent a pyrrolidino, piperidino or morpholino group, and wherein $R^1$ represents alkyl or alkenyl having from 1 to 7 carbon atoms, benzyl or benzyl substituted by one halogen atom or one alkoxy group having from 1 to 4 carbon atoms, are advantageously produced by the reaction of the corresponding 1H-pyrazol having the general Formula V

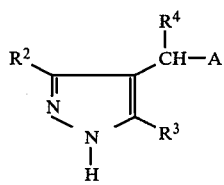

wherein $R^2$, $R^3$, $R^4$ and A have the significance set out hereinabove in Section (j), with an alkylation agent of the formula $R^1Q$, wherein $R^1$ has the significance set out hereinabove in Section (j) and Q represents the radical of a strong acid, preferably a halogen atom or alkylsulfonyl or p-tolylsulfonyl.

Where desired, the salts of the compounds, obtained by the embodiments (a) to (j) of the new method, may be readily produced by reacting the compounds with a pharmacologically acceptable inorganic or organic base. Difficulty soluble salts are preferably produced from the readily soluble salts by the reaction with the corresponding desired base.

The production of the pyrazol-4-acetic acids of the general Formula I, wherein A is —COOH, by hydrolysis of the respective functional derivatives, as set out hereinbefore in Section (a), may be effected in the usual manner in a neutral, acid or alkaline reaction medium, if necessary at elevated temperatures, preferably at temperatures between 50° and 150° C. and most advantageously at the boiling temperature of the solvent used in the reaction. If necessary, the reaction is benefically effected in the presence of a solvent adjuvant, such as a lower alcohol, dioxane or acetone. The hydrogenolysis of the benzyl esters to the free acids is advantageously carried out under the conventional conditions, e.g. with hydrogen on palladium carbon at room temperature in an inert solvent, such as methanol, ethyl acetate and/or glacial acetic acid. The thermolysis of the tert.-alkylesters to the free acids is effected preferably by heating of the tert.-alkylester of the respective compound in an inert organic solvent, such as benzene, advantageously in the presence of an acid catalyst, such as p-toluene sulfonic acid. The purification of the pyrazol-4-acetic acids produced in this manner is preferably effected by the extraction of an alkaline aqueous solution of the respective acetic acid compounds with an organic solvent, such as ether, benzene, chlorobenzene, chloroform or methylene chloride.

The synthesis of the pyrazol derivatives of the general Formula I with the various significance of the substituents $R^1$, $R^2$, $R^3$ and $R^4$ in accordance with the embodiment of the method set out in Section b) above is especially beneficial and generally results in relatively high yields of the desired compound. Because of the ready preparative accessibility of the reaction with compounds of the general Formulae II and III, in which A represents alkoxycarbonyl or benzyloxycarbonyl, this route is generally preferred. Because of the known mechanism of the reaction of γ-keto-carboxylic acids and their derivatives, as described e.g. by T. L. Jacobs in Elderfield, Heterocyclic Compounds, page 116, John Wiley and Sons, 1957, it was not expected that the pyrazol-4-acetic acid derivatives of the general Formula I be formed.

The reaction proceeds with high yields and may be effected in the absence of a solvent, or, if desired, in the presence of an inert solvent, such as the lower alcohols, hydrocarbons, chlorinated hydrocarbons, ethers of the lower alkyl ethers of ethylene glycol or of diethylene glycol of the lower aliphatic carboxylic acids, dimethylformamide, or N-methylpyrrolidine. Generally, the reaction may be effected at temperatures between 0° to 200° C., and preferably at temperatures between 50° and 150° C., and most advantageously at the boiling temperature of the solvent used in the reaction. The reaction is advantageously catalyzed by proton donors, such as glacial acetic acid. Generally, the reaction is completed in about 0.5 to 3 hours. In the case of the reaction of 3,3-diaroyl(heteroaroyl)-propionic acid esters of the general Formula II with aryl hydrazines of the general Formula IV, the raction mixture which preferably contains glacial acetic acid as a solvent is heated preferably for 4 to 7 hours to the boiling temperature of the glacial acetic acid. The components of the reaction are generally employed in equivalent proportions, though it is often advantageous, to employ the lesser costly component, usually the hydrazine, in a slight excess. The reaction products are beneficially isolated from the reaction mixture by evaporation of the solvent, and distillation or recrystallization of the residue, as the case may be.

The production of the pyrazol-4-acetonitriles of the general Formula I, wherein A is —CN, by the reaction of the corresponding halogen alkyl pyrazole, wherein A is Hal, with cyanides in accordance with the embodiment of the method set out hereinabove in Section (c) in preferably effected in polar solvents such as mixtures of alcohol and water, dimethylformamide, N-methylpyrrolidone or dimethyl sulfoxide, at temperatures ranging between 0° and 100° C., and most preferably at temperatures ranging from 10° to 50° C. The dehydration of the corresponding amides to the nitriles of the general Formula I, wherein A is —CN, is preferably carried out with $POCl_3$, $P_2O_5$, $PCl_5$ or $SOCl_2$ in an inert solvent, such as 1,2-dichloroethane, or if desired, without a solvent. The dehydration reaction may be carried out at room temperature or at elevated temperatures, preferably at a temperature ranging from 50° to 150° C.

The esters of the general Formula I, wherein A is —$COOR^6$ are produced, as stated above, by the embodiment of the method set out in Section (d) above. Examples of this method are e.g. azeotrope or extractive esterification of the corresponding free acid with an excess of the desired alcohol in the presence of a proton donor, reaction of the components at room temperature in the presence of dicyclohexyl carbodiimide, or the conversion of the free acid into the corresponding acid halogenide, for example by reaction with $POCl_3$, $SOCl_2$, $PCl_5$ or $PBr_3$, or by conversion into the corresponding acid anhydride, and reaction of the acid halogenide or anhydride with the alcohol, with or without the use of a basic condensation agent to form the desired ester.

The partial hydrolysis of the nitriles of the general Formula I, wherein A is —CN, to form the corresponding acid amides in accordance with the embodiment of the method set out in Section (e) above, may be effected e.g. by the reaction of the respective nitrile with concentrated sulfuric acid at room temperature or with alkaline hydrogen peroxide at a temperature ranging from 20° to 70° C.

The alcoholysis of the just mentioned nitriles in accordance with the embodiment of the method of the invention set out hereinbefore in Section (g) may advantageously be effected by treating the respective nitrile with alcohol and gaseous hydrochloric acid in the absence of water to form the corresponding imide acid ester hydrochloride, which is further hydrolyzed under mild conditions to result in the respective carboxylic acid water. The reaction can also be carried out in the presence of water to produce directly the corresponding carboxylic acid ester.

The acid amides may also be produced by the reaction of reactive acid derivatives with amines in accordance with the embodiment of the invention set out hereinbefore in Section (f), e.g. by reacting the corresponding acid halogenides in an aqueous or organic medium with two equivalents of the desired amine, or with one equivalent of the amine in the presence of an auxiliary base, such as an alkali metal hydroxide or pyridine. The acid amide may also be produced by reacting the corresponding acid with the desired amine in the presence of dicyclohexyl carboxiimide at room temperature, for instance, in methylene chloride or tetrahydrofuran as the solvent. The acid amides of the invention may also be produced by reaction of the corresponding ester with the desired amine at a temperature preferably in the range from 20° to 200° C. and most advantageously at a temperature in the range from 50° to 160° C., if desired in the presence of an inert solvent, such as a lower alcohol, if desired under pressure in a suitable pressure vessel.

The hydroxamic acids may be produced in accordance with the embodiment of the method of the invention set out in Section (h) above. Generally, in this embodiment of the method, one can follow in principle the procedure set out above in connection with the production of the acid amides in accordance with embodiment (f) of the method. It is, however, generally preferred to produce the hydroxamic acids by the reaction of the corresponding carboxylic halogenides with hydroxylamine in the presence of an auxiliary base, such as pyridine, preferably at a temperature ranging from 0° to 30° C.

The reaction of the 1H-pyrazols of the Formula V in accordance with the embodiment of the method set out in Section (j) above, with an alkylation agent of the Formula $R^1Q$ is advantageously effected at a temperature between 0° and 100° C., and preferably at a temperature between 20° and 50° C., if desired in the presence of a solvent, such as aromatic hydrocarbons, alcohols or aprotic dipolar solvents, such as dimethylformamide, N-methylpyrrolidone or dimethylsulfoxide. The reaction is preferably carried out in the presence of a basic condensation agent, such as alkali metal or alkaline earth metal, the hydroxides, hydrides, amides or carbonates of these metals or in the presence of organic nitrogenous bases, such as pyridine or triethylamine. The alkylation agent of the Formula $R^1Q$ is generally employed in a 1–1.2 molar amount based on the 1H-pyrazol.

The salts of the acid compounds of the invention with non-toxic inorganic or organic bases may be produced by dissolving the free acids in an aqueous or organic medium and thereafter adding the required amount of the desired base. Suitable cations for the formation of the salts comprise monovalent and polyvalent metals, such as lithium, sodium, potassium, magnesium, calcium and aluminum and protonated or quaternated organic nitrogenous bases, such as ammonia, ethanolamine, diethanolamine, triethanolamine, ethylene diamine, glycosamine or N-methyl glucosamine.

The compounds of the general Formulae II and III may be produced by a variety of methods. So, for instance, 3,3-diacetylpropionic acid may be produced by the reaction of α-angelica lactone, acetic acid anhydride and fluoroborate ether as described by *Suomen Kemistilehti*, 28, B 87 (1955). 3,3-diacetylpropionic acid-ethylester may be produced by the alkylation of acetylacetone with bromoacetic acid-ethyl ester as described in *J. Chem. Soc.* 1958, 4254. Under further improved conditions, also other β-diketones may be alkylated by this method in the α-position in high yields, using bromo acetic acid ethylester or other derivations of lower α-halogen alkanoic acids, such as with α-bromopropionic acid-ethyl ester. The 4-dialkylamino-3-acylbutene-3-acid derivatives of the general Formula III are new and no described in the literature. They may be produced e.g. by the reaction of 3,3-diacylpropionic acid derivatives with the desired dialkylamine or by the acylation of 3-acylproionic acid derivatives in the 2-position, for example, with amide acetals or aminic esters. The 4-alkoxy-3-acyl-butene-3-acid derivatives and the 4-acyloxy-3-acyl-butene-3-acid derivatives may be obtained by the alkylation or acylation, respectively, of the corresponding enolized 3,3-diacyl propionic acid derivatives.

Halogen alkylpyrazols of the general Formula I, wherein A is halogen can be produced from the corresponding hydroxy-alkylpyrazols of the general Formula I, wherein A is OH, for instance by the reaction with inorganic acid halogenides such as $SOCl_2$, if desired in the presence of catalytic amounts of pyridine or dimethylformamide, or with $PCl_3$ or $PCl_5$. In those cases, where $R^4$ is hydrogen in the general Formula I of the desired halogen alkylpyrazol, the halogen alkylpyrazol may also be produced by direct chloromethylation of the corresponding pyrazol, which is unsubstituted in the 4-position. The hydroxyalkylpyrazols may, in turn, be produced from the corresponding carbonyl derivatives, e.g. by reacting with sodium borohydride. The corresponding pyrazol-4-acetic acid thioamides can be produced by reacting the corresponding 4-acetyl pyrazols with the desired amines and with sulfur.

An important modification of the method of the invention comprises the carrying out of successive method steps without isolation or purification of the intermediate products. So, for instance, may the steps of alkylation of the β-dicarbonyl compounds with the formation of the corresponding 3,3-diacyl-propionic acid esters of the general Formula II, the reaction of this intermediate product with the desired hydrazine to form the corresponding pyrazol-4-acetic acid esters and the hydrolysis of this product to form the desired pyrazol-4-acetic acid be carried out successively with the respective reaction mixtures, without isolation of the intermediate products, whereby the desired pyrazol-4-acetic acid is obtained in high yield and of excellent purity. This modification of the method of the invention may also beneficially be employed in the succession of steps in the reaction for making 4-halogenalkylpyrazol, pyrazol-4-acetonitrile and pyrazol-4-acetic acid, in this order.

The new pyrazol-4-acetic acid compounds of the general Formula I and their pharmacologically acceptable salts, are mostly crystalline solids, some are high boiling liquids. The free acid is usually soluble in aqueous alkali. The new pyrazol-4-acetic acids and derivatives and their pharmacologically acceptable salts are useful for administration to warm blooded animals.

The following examples illustrate the invention, but are not to be construed as limiting the same. The temperature values given herein are in degrees Centigrade. Melting points are designated by the letters M.P. and boiling points at 10 Toor are designated by $Kp_{10}$.

EXAMLE 1

(a) 3.7 grams 3,3-diacetyl-propionic acid ethyl ester, 1.2 grams glacial acetic acid and 2.2 grams phenylhydrazine were mixed with 40 milliliters ethanol and the mixture heated to the boiling temperature under reflux for 2 hours. The mixture was then evaporated in vacuo and the concentrated residue mixed, with rubbing wth petroleum ether. The precipitate was filtered off by suction and twice recrystallized from the ethanol/water mixture. 4.1 grams 3,5-dimethyl-1-phenyl-pyrazol-4-acetic acid ethyl ester melting at 86°–87° C. and representing a yield of 81% were obtained.

the 3,3-diacetyl-propionic acid ethyl ester used in the foregoing example as the starting material was produced in the following manner:

60 grams acetylacetone were mixed with a mixture of 120 milliliters water and 140 milliliters dioxane. To this mixture was added dropwise at 20° C. and with cooling a solution of 33.6 grams potassium hydroxide in 30 milliliters water. Thereafter, 101 grams bromoacetic acid ester were slowly added dropwise at the same temperature over a period of 3 hours. The reaction mixture was then stirred for 20 hours at room temperature, evaporated in vacuo and the concentrated solution extracted ether. The ether extract was dried over anhydrous magnesium sulfate and distilled in a column. 3,3-Diacetyl-propionic acid ethyl ester, having a $Kp_{10}$ of 125°–127° C. was obtained in a yield of 45%.

(b) 3.5 grams of the 3,5-dimethyl-1-phenyl-pyrazol-4-acetic acid ethyl ester obtained in Example 1a) above, 1.0 gram sodium hydroxide, 10 milliliters water and 10 milliliters ethanol were mixed and the mixture heated to boiling temperature under reflux for 15 minutes. The solution thus obtained was of the adjusted till it reached a value of 9–10. Thereafter the alcohol was distilled off and the aqueous solution was extracted with ether or benzene and the aqueous solution was clarified by treatment with activated carbon. After acidifying the clear aqueous solution with hydrochloric acid, 2.7 grams 3,5-dimethyl-1-phenyl-pyrazol-4-acetic acid, melting at 137°–139° C. were obtained, representing a yield of 86%. After recrystallization from a mixture of water and methanol, the acid melted at 138°–139° C.

(c) 10 grams of a 50% suspension of sodium hydride in paraffin oil were disposed in 100 milliliters dimethyl formamide and to the dispersion, thus obtained, 20 grams acetylacetone were added drop by drop. After completion of the evolution of hydrogen, 31 grams bromoacetic acid methyl ester were added dropwise with stirring to the reaction mixture at room temperature and the mixture was stirred for another 15 hours. The solvent was then distilled off, the residue was taken up in ether, and the ether solution extracted with water. By distillation of the ether solution 26 grams of crude, 3,3-diacetylpropionic acid-methyl ester having a $Kp_{10}$ of 112°–117° C. were obtained. The distilled 3,3-diacetyl-propionic acid methylester was reacted with 16.5 grams phenylhydrazine and 9 grams glacial acetic in 100 milliliters ethanol and the reaction product was recovered by the method described in Example (1a) above, 28 grams of crude, 3,5-dimethyl-1-phenyl-pyrazol-4-acetic acid methyl ester were obtained, which, after recrystallization from a mixture of ethanol and water, melted at 63°–64° C.

By saponofication of the ester in a manner as described in Example (1b) above, 24 grams 3.5-dimethyl-1-phenyl-pyrazol-4-acetic acid were obtained, having a M.P. of 137°–139° C. and representing a yield of 52% based on acetylacetone.

(d) 3 grams 3,5-dimethyl-1-phenyl-pyrazol-4-acetamide (M.P. 169°–170° C.) were mixed with 30 milliliters 25% aqueous hydrochloric acid and heated to boiling temperature under reflux for 0.5 hour. 2.5 grams 3,5-dimethyl-1-phenyl-pyrazol-4-acetic acid, melting at 137°–139° C. and representing a yield of 83%, were obtained after recovery at a pH of 4–5 from the reaction mixture in accordance with the general procedure described in the Example above.

(e) 3,5-dimethyl-1-phenyl-pyrazol-4-acetonitrile (M.P. 69°–70° C.) was saponified in 25% aqueous hydrochloric acid in accordance with the procedure described in Example 1d) above. 3,5-dimethyl-1-phenyl-pyrazol-4-acetic acid, having a M.P. of 138°–139° C., was obtained in a yield of 92%.

(f) 6 grams 3,5-dimethyl-1-phenyl-4-acetylpyrazol (Grandberg et al., C.A. 63, 16332 f (1965), 1.0 gram sulfur and 4.5 grams morpholine were mixed and the mixture heated to the boiling temperature under reflux for 10 hours. The reaction mixture was then poured on ice and the crude 3,5-dimethyl-1-phenylpyrazol-4-thioacetmorpholide thus obtained and separated was hydrolyzed by boiling with 60 milliliters 20% aqueous hydrochloric acid. After filtration and working up by the procedure described above 4.4 grams 3,5-dimethyl-1-phenyl-pyrazol-4-acetic acid, melting at 136°–137° C., were obtained, representing a yield of 67%.

EXAMPLE 2

(a) 80.0 grams 3,3-dibenzoyl-propionic acidethyl ester, 32.0 grams phenylhydrazine and 20 grams glacial acetic acid were mixed and the mixture heated in a nitrogen atmosphere to boiling temperature under reflux for 6.5 hours. The main portion of the acetic acid was then distilled off, and the residue dissolved in 700 milliliters benzene. The benzene solution was extracted with water. The benzene was distilled off the benzene solution and the residue mixed with 300 milliliters ethanol, 300 milliliters water and 20 grams sodium hydroxide and the mixture heated to the boiling temperature under reflux for one hours. Thereafter the alcohol was distilled off, and the remaining aqueous mixture diluted with water to make about 1 liter, followed by extraction with benzene and clarification of the aqueous phase by boiling with activated carbon. The clear solution was then acidified until the pH of 3 was achieved. The acidified mixture was then briefly stirred at a temperature of 50°–60° C., and the precipitate formed thereby was filtered by suction and washed with warm water. 81 grams 1,3,5-triphenyl-4-acetic acid, melting at 210°–212° C., and representing a yield of 89%, were obtained. By recrystallization from a mixture of methanol and water, the melting point increased to 211°–212° C.

(b) The 3,3-dibenzoyl-propionic acid ethyl ester required as the starting material in the foregong Example 2(a) was produced in the following manner: A solution of 100 grams 1,3-diphenyl-1,c-propane-dion in 200 milliliters dimethyl-formamide was added dropwise at room temperature to 21.5 grams of a 50% suspension of sodium hydride in paraffin oil dispersed in 400 milliliters dimethyl formamide. After completion of the evolution of hydrogen, 82 grams bromoacetic acid ethyl ester were added to the reaction mixture at room temperature, followed by stirring of the mixture for 20 hours at room temperature. The dimethyl-formamide solvent was then distilled off, the residue was taken up in benzene and the solution, after adjusting it to a pH of 4, was extracted with water. The benzene solution was dried, evaporated and the substance was recrystallized from a mixture of cyclohexane and petroleum ether of a boiling range of 50°–70° C. 115 g of 3,3-dibenzoyl-propionic acid ethyl ester, melting at 81°–83° C., were obtained, representing a yield of 83%.

By another recrystallization of the product from the above stated cyclohexane/petroleum ether solvent mixture, the melting point was increased to 83°–84° C.

(c) The procedure of Example (2a) above was repeated, using the crude evaporated benzene solution of the 3,3-dibenzoyl-propionic acid ethyl ester obtained in Example (2b) above, without further purification and recrystallization, as the starting material, which material was directly reacted with phenylhydrazine and glacial acetic acid and worked up in the manner described in Example (2a) above. 1,3,5-Triphenylpyrazol-4-acetic acid, having a melting point of 210°–212° C. was obtained in this manner in a yield of 76%, based on the 1,3-diphenyl-1,3-propane-dion starting material.

EXAMPLE 3

(a) 6.1 grams 3,4-dimethoxy-phenyl hydrazinehydrochloride, 5.6 grams, 3,3-diacetyl-propionic acidethyl ester and 2.5 grams anhydrous sodium acetate were mixed with 50 milliliters ethanol and the mixture was heated to the boiling temperature under reflux for 3 hours. The reaction mixture was then evaporated and the residue was taken up in ether, followed by two extractions with water, the first extraction was carried out at a pH of 5 and the second extraction at a pH of 9. After removal of the ether, the organic phase was distilled, resulting in 6.0 grams of an oil having a $Kp_{0.01}$ of 187°–190° C. The oil, which crystallized, was recrystallized from a mixture of toluene and petroleum ether. 4.8 grams 3,5-dimethyl-1-[3,4-dimethoxyphenyl-(1)]-pyrazol-4-acetic acid-ethyl ester, melting at 55°–56° C. were obtained, representing a yield of 50%.

(b) 3.0 grams of the 3,5-dimethyl-1-[3,4-dimethoxy pheyl-(1)]-pyrazol-4-acetic acid-ethyl ester produced in accordance with the method of Example (3a) were mixed with a solution of 0.8 gram potassium hydroxide in 25 milliliters water and 25 ml ethanol and saponified and worked up by the method described in Example (1b). 2.4 grams of 3,5-dimethyl-1-[3,4-dimethoxy-pheny-(1)]-pyrazol-4-acetic acid, melting at 171°–172° C. were obtained, representing a yield of 88%.

EXAMPLE 4

(a) 8.0 grams p-tolylhydrazine-hydrochloride, 9.3 grams 3,3-diacetyl-propionic acid-ethyl ester, 4.1 grams anhydrous sodium acetate and 70 milliliters ethanol were mixed and the mixture was heated to the boiling temperature under reflux for 1.5 hour. The reaction mixture was worked up as described in Example (3a). After distillation, 12.1 grams 3,5-dimethyl-1-(p-tolyl)-pyrazol-4-acetic acid-ethyl ester were obtained as a viscous oil having a $Kp_{0.001}$ of 145°–146° C., representing a yield of 89%. For analysis, the product was redistilled resulting in an $n^{20}_D$ 1.5455.

(b) 8.2 grams of the 3,5-dimethyl-1-(p-tolyl)-pyrazol-4-acetic acid-ethyl ester, produced by the method of Example (4a), were mixed with a solution of 2.5 grams potassium hydroxide in 15 milliliters water and 15 milliliters ethanol, and the ester saponified and the free acid isolated by the method described in Example (1b). 6.0 grams of 3,5-dimethyl-1-(p-tolyl)-pyrazo-4-acetic acid, melting at 119°–121° C. were obtained, representing a yield of 82%.

EXAMPLE 5

14.9 grams 3,3-diacetyl-propionic acid-ethyl ester, 14.1 grams ($\alpha,\alpha,\alpha$-trifluoro-m-tolyl)-hydrazine, 4.8 grams glacial acetic acid and 100 milliliters ethanol were mixed, and the mixture heated to boiling temperature under reflux for 1 hour. The reaction mixture was evaporated and the residue distilled to produce 22.3 grams of crude 3,5-dimethyl-1-($\alpha,\alpha,\alpha$-trifluoro-m-tolyl)-pyrazol-4-acetic acid ethyl ester. This ester was saponified aas and worked up in accordance with the method described in Example (1b), using 4.0 grams sodium hydroxide as the base. The free acid was precipitated from the alkaline solution obtained in this manner by the addition of 2% acetic acid and of sufficient aqueous hydrochloric acid to complete the precipitation.

In this manner, 18.4 grams 3,5-dimethyl-1-($\alpha,\alpha,\alpha$-trifluoro-m-tolyl)-pyrazol-4-acetic acid having a melting point of 80°–92° C. were obtained, representing a yield of 77%, based on the 3,3-diacetyl-propionic acid-ethyl ester starting material. After recrystallization from diluted aqueous acetic acid the substance had a melting point of 83°–85° C.

EXAMPLE 6

(a) 9.3 grams 3,3-diacetyl-propionic acid-ethyl ester, 8.7 grams p-methoxy phenyl-hydrazine-hydrochloride, 4.9 grams anhydrous sodium acetate and 90 milliliters ethanol were mixed and the mixture heated to boiling temperature under reflux for 2.5 hours. The reaction mixture was thereafter evaporated and ether added to the residue. The ether phase was extracted with water and the ether evaporation. The crystalline residue was recrystallized twice from a mixture of ethanol and water. 9.2 grams 3,5-dimethyl-1-(p-methoxy phenyl)-pyrazol-4-acetic acid-ethyl ester, melting at 71°–72° C. were obtained, representing a yield of 64%.

(b) 8.0 grams of 3,5-dimethyl-1-(p-methoxy phenyl)-pyrazol-4-acetic acid-ethyl ester produced by the method of Example (6a) were added to a mixture of sodium hydroxide and ethanol and the ester saponified and precipitated by the method described in Example (2b).

The free acid thus obtained was purified by redissolving it in aqueous sodium hydroxide solution, and by precipitating it therefrom by the addition of sufficient aqueous hydrochloric acid.

6.1 grams 3,5-dimethyl-1-(p-methoxy-phenyl)-pyrazol-4-acetic acid melting at 154°–155° C. were obtained, representing a yield of 84%.

EXAMPLE 7

4.0 grams 3,3-diacetyl-propionic acid, 4.9 grams p-chlorophenylhydrazine-sulfate, 2.1 grams anhydrous sodium acetate and 30 milliliters glacial acetate acid were mixed and the mixture was heated to 60° C. for 3 hours. The reaction mixture was evaporated and water was added to the residue. The precipitate formed thereby was separated by filtration and recrystallized from a mixture of ethanol and of water. 5.5 grams 3,5-dimethyl-1-(p-chlorophenyl)-pyrazol-4-acetic acid, melting at 176°–177° C., were obtained, representing a yield of 82%.

EXAMPLE 8

3,3-diacetyl-propionic acid, m-chloro-phenyl hydrazine-sulfate and anhydrous sodium acetate were reacted and worked up by a procedure analogous to that described in Example 7. 3,5-Dimethyl-1-(m-chlorophenyl)-pyrazol-4-acetic acid, having a melting point of 132° C., was obtained in a yield of 87%.

EXAMPLE 9

(a) 18.6 grams 3,3-diacetyl-propionic acid-ethyl ester, 9.0 grams glacial acetic acid and 150 milliliters methanol were mixed, and 5.3 grams hydrazine hydrate were added dropwise to this mixture within 30 minutes. The reaction mixture was then heated to the boiling temperature under reflux for 3 hours. The reaction mixture was then evaporated and distilled in vacuo. The fraction obtained at 142°–150° C./0.05 Torr consisted of an oil which later crystallized. 16.2 grams 3,5-dimethyl-1H-pyrazol-4-acetic acid-ethyl ester were obtained, representing a yield of 80%.

By chromatographic purification and redistillation, and the melting point increased to 39°–40° C.

(b) 3.6 grams 3,5-dimethyl-1H-pyrazol-4-acetic acid-ethyl ester obtained by Example (9a) and 20 milliliters 2n aqueous sodium hydroxide solution were mixed, and the mixture heated to the boiling point under reflux for 30 minutes. The solution was then clarified by filtration, and evaporated to about one half its volume. The concentration solution was then acidified by the dropwise addition of concentrated aqueous hydrochloric acid, until it had a pH of 4, with cooling by ice. The precipitate was separated by filtration. 2.5 grams 2,5-dimethyl-1H-pyrazol-4-acetic acid, melting at 191°–192° C., were obtained, representing a yield of 81%.

EXAMPLE 10

(a) 10.9 grams 3,5-dimethyl-1H-pyrazol-4-acetic acid-ethyl ester produced in accordance with the method of Example 9a) were incorporated into a solution of 1.4 gram sodium in 20 milliliters methanol. The solution thus obtained was evaporated in vacuo and the residue was taken up in 50 milliliters 1,2-dimethoxy ethane. 15 g n-butyl-bromide were added thereto, and the mixture was heated to boiling temperature under reflux for 5 hours. Thereafter the reaction mixture was evaporated, the residue taken up in ether followed by extraction with dilute aqueous sodium carbonate solution. The ether phase was then dried over calcium chloride and the ether evaporated. Distillation of the residue resulted in 10 grams 3,5-dimethyl-1-n-butyl-pyrazol-4-acetic acid-ethyl ester, having a $Kp_{0.001}$ of 86°–87° C., representing a yield of 70%.

(b) The 3,5-dimethyl-1-n-butyl-pyrazol-4-acetic acid-ethyl ester produced by the method of Example (10a) was saponified and the free acid recovered in accordance with the method described in Example 1b). 3,5-Dimethyl-1-n-butyl pyrazol-4-acetic acid was obtained in a yield of 91% and having a melting point of 97°–98° C.

EXAMPLE 11

(a) 2.6 grams of a 50% suspension of sodium hydride in paraffin oil were dispersed in 30 milliliters absolute dimethylformamide and a solution of 9.1 grams 3,5-dimethyl-1H-pyrazol-4-acetic acid-ethyl ester in 10 milliliters dimethylformamide was added dropwise at room temperature to the sodium hydride suspension. The reaction mixture was stirred, without heating, until the evolution of hydrogen subsided (about 15 minutes). Thereafter, a solution of 10 grams isoamylbromide in 10 milliliters dimethylformamide was added dropwise during 30 minutes to the reaction mixture. The mixture was then stirred for 15 hours at room temperature and an additional 3 hours at 40° C. The reaction mixture was then neturalized and the solvents were distilled off in vacuo. To the residue were added about 70 milliliters water and the pH was adjusted to 10. The aqueous phase was then extracted with ether. The ether was evaporated, after drying, from the ether phase and the residue distilled to result in 10.2 grams 3,5-dimethyl-1-iso-amyl-pyrazol-4-acetic acid-ethyl ester, representing a yield of 81%. The substance had a $Kp_{0.001}$ of 96°–99° C.

(b) The 3,5-dimethyl-1-iso-amyl-pyrazol-4-acetic acid-ethyl ester produced by the method of Example 11a) was saponified and the free acid recovered in accordance with the method described in Example 1b). 3,5-Dimethyl-1-iso-amyl-pyrazol-4-acetic acid, melting at 135°–136° C., was obtained in a yield of 78%.

EXAMPLE 12

(a) 8.0 grams 3,5-dimethyl-1H-pyrazol-4-acetic acid-ethyl ester, provided by the method of Example (9a) were reacted with 2.2 grams of a 50% sodium hydride suspension in paraffin oil and with 7.0 grams allyl-bromide in a procedure analogous to that described in Example (11a). 8.7 grams 3,5-dimethyl-1-allyl-pyrazol-4-acetic acid-ethyl ester, having a $Kp_{0.001}$ of 79°–82° C. were obtained, representing a yield of 89%.

(b) 5 grams of 3,5-dimethyl-1-allyl-pyrazol-4-acetic acid-ethyl ester were mixed with 25 milliliters methanol and 10 milliliters water. The mixture was heated to the boiling temperature and held there while 11.3 milliliters 2n aqueous sodium hydroxide were added dropwise at such rate, that the pH of 10 was maintained. The reaction mixture thus obtained was worked up by the procedure described in Example (1b). 21. grams 3,5-dimethyl-1-allyl-pyrazol-4-acetic acid melting at 139°–140° C. were obtained representing a yield of 48%.

EXAMPLE 13

9.1 grams 3,5-dimethyl-1H-pyrazol-4-acetic acid-ethyl ester produced in accordance with the method of Example 9a) were added in portions and with light cooling to a mixture of 1.27 gram pure sodium hydride and 70 milliliters 1,2-dimethoxyethane. After completion of the gas formation, 10.0 grams benzyl chloride were added dropwise over the time period of 1 hour. The reaction mixture was then stirred for 3 hours at room temperature and thereafter for 24 hours at boiling temperature under reflux. The solution thus obtained was filtered and evaporated. The crude pyrazol acetic ester thus obtained was mixed with 70 milliliters methanol and 80 milliliters 1 N aqueous sodium hydroxide and the mixture was heated to the boiling temperature under reflux for 15 minutes. The reaction mixture was worked up and the free acid recovered in the manner described in Example (1b). 7.3 grams 3,5-dimethyl-1-benzyl-pyrazol-4-acetic acid, melting at 119°–121° C., were obtained, representing a yield of 60%. After recrystallization from a mixture of ethanol and water, the melting point was 120°–122° C.

EXAMPLE 14

3,5-Dimethyl-1H-pyrazol-4-acetic acid-ethyl ester produced by the method of Example (9a) was alkylated by reaction with p-chlorobenzyl chloride and sodium hydride in dimethyl formamide at room temperature and subsequently saponified by a method similar to that described in Example 13.

3,5-Dimethyl-1-(p-chlorobenzyl)-pyrazol-4-acetic acid, melting at 173°–174° C., was obtained in a yield of 65%.

EXAMPLE 15

(a) 4.1 grams 4-hydrazinobiphenyl obtained by the method described by H. Niwa in C.A. 52, 7233 f (1958), 4.1 grams 3,3-diacetyl-propionic acid-ethyl ester, 1.3 gram clacial acetic acid and 30 milliliters ethanol were mixed and the mixture was heated for 3 hours to the boiling temperature under reflux. Thereafter, 25 milliliters 2n aqueous sodium hydroxide were added to the reaction mixture, which was then heated for another 30 minutes under reflux to the boiling temperature. The mixture was then adjusted to a pH of 9–10 and the ethanol was distilled off, the residue diluted with water, the aqueous solution cleared by treatment with activated carbon. The clear solution was then acidified to a pH of 4. The precipitate formed there by was filtered off and recrystallized first from a mixture of methanol and water and thereafter from coluene. 5.1 grams 3,5-dimethyl-1-(p-biphenylyl)-pyrazol-4-acetic acid, melting at 158°–160° C. were obtained, representing a yield of 77%.

(b) In another modification of the method described in Example (15a) the starting materials and components and quantities listed in Example (15a) were heated to boiling temperature for 3 hours. the solution thus obtained was evaporated in vacuo and 30 milliliters 25% aqueous hydrochloric acid were added thereto. The acid mixture was heated to the boiling temperature under reflux for 2 hours. The pH of the solution was adjusted to 4. The precipitate formed thereby was recovered and purified as described in Example (15a). 3,5-Dimethyl-1-(p-biphenylyl)-pyrazol-4-acetic acid was obtained in a yield of 72%. The substance had a melting point of 157°–159° C.

EXAMPLE 16

3.0 grams 3-benzoyl-levulinic acid-ethyl ester, 1.3 gram phenyl-hydrazine, 0.15 milliliter 2n aqueous hydrochloric acid and 25 milliliters n-butanol were mixed and the mixture heated to boiling temperature under reflux for 1.5 hour. The reaction mixture was evaporated in vacuo and benzene added to the residue. The benzene solution was adjusted to a pH of 4 and extracted with water. The benzene was evaporated from the solution, and 15 milliliters ethanol and 20 milliliters 1n aqueous sodium hydroxide were added to the residue and the mixture was heated to the boiling temperature. The mixture was then worked up and the free acid recovered in accordance with the procedure set out in Example (1b). 3,3 grams 3-methyl-1,5-diphenyl-pyrazol-4-acetic acid, melting at 159°–161° C., were obtained representing a yield of 93%.

After recrystallization from a mixture of ethanol and water, the substance had a melting point of 163°–164° C.

The 3-benzoyl-levulinic acid ethyl ester used as the starting material in Example 16 was produced by the alkylation of benzoyl acetone dissolved in absolute dimethyl formamide with a slight excess of bromoacetic acid ethyl ester in the presence of sodium hydride. The 3-benzoyl-levulinic acid ethyl ester was obtained in a yield of 79% and had a $Kp_{0.03}$ of 140°–141° C.: n 20/d 1.5196.

EXAMPLE 17

3.7 grams 3-benzoyl-levulinic acid ethyl ester, 2.9 grams m-chlorophenyl-hydrazine-sulfate, 1.2 grams sodium acetate and 45 milliliters n-butanol were mixed and the mixture heated to the boiling temperature under reflux for 1.5 hour. The reaction mixture was then evaporated in vacuo. To the residue, representing the crude ester, were added 20 milliliters ethanol and 22 milliliters 1n aqueous sodium hydroxide and the ester saponified and the free acid recovered by the procedure described in Example (1b). 3.7 grams 3-methyl-5-phenyl-1(m-chlorophenyl)-pyrazol-4-acetic acid, having a melting point of 147°–149° ., were obtained, representing a yield of 75.5%.

EXAMPLE 18

3-benzoyl-levulinic acid ethyl ester and p-chlorophenylhydrazine-sulfate were reacted and worked up in accordance with the procedure set out in Example 17. 3-methyl-5-phenyl-1-(p-chlorophenyl)-pyrazol-4-acetic acid, having a melting point of 153°–154° C., was obtained in a yield of 73.5%.

EXAMPLE 19

(a) 6.7 grams 3-benzoyl-levulinic acid ethyl ester, 5.0 grams 4-hydrazinobiphenzyl, 1.6 gram glacial acetic acid and 50 milliliters n-butanol were mixed and the mixture heated to the boiling temperature under reflux for 3 hours. The reaction mixture was evaporated and the residue was taken up in ether, and extracted twice with water first at a pH of 4–5 and thereafter at a pH of 9–10. The ether was then removed from the ether phase by evaporation and the crystalline residue was recrystallized from a mixture of petroleum ether boiling in a range from 100°–140° C. and ethyl acetate. 6.7 grams 3-methyl-5-phenyl-1-(p-biphenylyl)-pyrazol-4-acetic acid-ethyl ester, having a melting point of 105°–107° C., were obtained, representing a yield of 62%. After recrystallization of the substance from petroleum ether boiling in a range from 100°–140° C. the melting point was 108°–109° C.

(b) The 3-methyl-5-phenyl-1-(p-biphenylyl)-pyrazol-4-acetic acid ethyl ester obtained in Example (19a) was saponified and the free acid recovered by the procedure described in Example (1b). 3-Methyl-5-phenyl-1-(p-biphenylyl)-pyrazol-4-acetic acid, melting at 255°–258° C., was obtained in a 84% yield.

EXAMPLE 20

11.5 grams 3-(p-chlorobenzoyl)-levulinic acid ethyl ester, 4.9 grams phenyl-hydrazine, 2.8 grams glacial acetic acid and 10 milliliters ethanol were mixed an the mixture was heated to the boiling temperature under reflux for 3.5 hours. The reaction mixture was evaporated and 100 milliliters benzene were added to the residue. The pH of the solution was adjusted to 3, followed by extraction with water. The benzene phase was evaporated and 30 milliliters ethanol and 20 milliliters 2n aqueous sodium hydroxide added to the residue. The mixture was heated to the boiling temperature under reflux for 1 hour, and thereafter worked up and the free acid recovered in accordance with a procedure analogous to that set out in Example (1b). 9.6 grams 3-methyl-1-phenyl-5-(p-chlorophenyl)pyrazol-4-acetic acid, melting at 174°–177° C., were obtained representing a yield of 72%.

The 3-(p-chlorobenzoyl)-levulinic acid ethyl ester used in Example 20 as the starting material was obtained in the following manner: p-chloro-acetophenone, acetic acid ethyl ester and sodium hydride were condensed to form p-chloro-benzoylacetone by the method described by Swamer and Hauser, J. Am. Chem. So. 72, 1352 (1952). The p-chlorobenzoylacetone thus obtained was alkylated by reaction with bromoacetic acid ester and sodium hydride in dimethyl formamide to produce 3-(p-chlorobenzoyl)-levulinic acid ethyl ester in a yield of 83%, having a boiling point $K_{p0.001}$ of 140°–150° C.

EXAMPLE 21

8.0 grams 3,3-dibenzoyl-propionic acid-ethyl ester, 5.9 grams p-chlorophenyl-hydrazine sulfate, 2.5 grams sodium acetate and 3.0 grams glacial acetic acid were reacted and the reaction product recovered by a procedure analogous to the method set out in Example (2a). 7.9 grams 3,5-diphenyl-1-(p-chlorophenyl)-pyrazol-4-acetic acid, melting at 193°–194° C. were obtained, representing a yield of 78%.

EXAMPLE 22

8.0 grams 3,3-dibenzoyl-propionic acid-ethyl ester, 5.5 grams o-chlorophenylhydrazine hydrochloride, 2.5 grams sodium acetate and 4.0 grams glacial acetic acid were reacted and the reaction product recovered by a procedure analogous to the method set out in Example 21. 3.7 grams 3,5-diphenyl-1-(o-chlorophenyl)-pyrazol-4-acetic acid, melting at 191°–193° C., were obtained, representing a yield of 37%.

EXAMPLE 23

(a) 6.0 grams 3,3-dibenzoyl-propionic acid-ethyl ester, 3.7 grams (α,α,α-trifluoro-m-tolyl)-hydrazine, 1.3 grams glacial acetic acid and 40 milliliters chlorobenzene were mixed and the mixture heated to the boiling temperature for 6 hours, whereby the water formed in the reaction was continuously distilled off. The reaction mixture was then extracted with water and the chlorobenzene evaporated from the chlorobenzene phase. The residue was chromatographically purified with the use of neutral silica gel and a mixture of ethyl acetate, benzene and cyclohexane as the flow agent. 5.3 grams 3,5-diphenyl-1-(α,α,α-trifluoro-m-tolyl)-pyrazol-4-acetic acid-ethyl ester, having a melting point of 73°–80° C., were obtained, representing a yield of 60%. After recrystallization from methanol, the substance had a melting point of 78°–80° C.

(b) 3,5-diphenyl-1-(α,α,α-trifluoro-m-tolyl)-pyrazol-4-acetic acid-ethyl ester produced in accordance with the method of Example (23a) was saponified and the free acid recovered in accordance with the procedure set out in Example (1b). 3,5-diphenyl-1-(α,α,α-trifluoro-m-tolyl)-pyrazol-4-acetic acid, melting at 166°–167° C. was obtained in a yield of 81%.

EXAMPLE 24

6.2 grams 3,3-dibenzoyl-propionic acid-ethyl ester, 1.0 gram methyl hydrazine and 4 grams glacial acetic acid were mixed and the mixture heated to the boiling temperature under reflux for 4 hours. The reaction mixture was then evaporated, the residue taken up in benzene and extracted with water. The benzene was then distilled from the benzene phase and the reside, consituting the crude ester reaction product, was heated with 2.0 grams sodium hydroxide, 20 milliliters ethanol and 20 milliliters water to the boiling temperature under reflux for 2 hours. The reaction mixture was then worked up and the reaction product was recovered by the general procedure set out in Example (2a). The recovered free acid was recrystallized from a mixture of benzene and petroleum ether boiling in a range from 50°–70° C. 3.9 grams 1-methyl-3,5-diphenyl-pyrazol-4-acetic acid, melting at 170°–172° C., were obtained, representing a yield of 67%.

EXAMPLE 25

(a) To a solution of 15 grams 3,3-dibenzoylpropionic acid ethyl ester and 3 grams glacial acetic acid in 90 milliliters ethanol was added at room temperature drop by drop a solution of 3.0 grams hydrazine hydrate in 10 milliliters ethanol followed by stirring at room temperature for 3 hours. The reaction mixture was then clarified by treatment with activated carbon, and 150 milliliters water were added to the clear solution followed by cooling in an ice bath. The precipitate formed thereby was filtered off by suction, dried and taken up in 400 milliliters benzene. The benzene solution was extracted first with a saturated aqueous solution of sodium bicarbonate and thereafter with water. The benzene solution was dried and benzene distilled off. By the addition of about three times this volume of cyclohexane, a precipitate representing the ester reaction product was formed which was separated by filtration. 13.1 grams 3,5-diphenyl-1H-pyrazol-4-acetic acid-ethyl ester melting at 117°–118° C. were obtained, representing a yield of 86%.

(b) 3 g 3,5-diphenyl-1H-pyrazol-4-acetic acid-ethyl ester produced in accordance with the method of Example (25a), 15 milliliters ethanol, 15 milliliters water and 3 grams sodium hydroxide were mixed and the mixture heated to the boiling temperature under reflux for 4 hours.

The free acid produced in this manner was recovered in the manner described above. 2.5 grams 3,5-diphenyl-1H-pyrazol-4-acetic acid, melting at 210°–211° C. was obtained, representing a yield of 92%.

EXAMPLE 26

5.0 grams 3,5-diphenyl-1H-pyrazol-4-acetic acid-ethyl ester produced in accordance with the method of Example (25a), 0.8 gram of a 50% suspension of sodium hydride in paraffin oil, 2.5 grams n-butylbromide and dimethylformamide were mixed and the mixture reacted for 5 hours at room temperature. The reaction mixture was then worked up in accordance with a procedure analogous to that set out in Example (11a) to recover the crude pyrazol acetic acid ester, to which was added a solution of 4.0 grams solium hydroxide in a 50% water-ethanol mixture. The pyrazol acetic acid ester was saponified and the free acid was recovered from the reaction mixture by a procedure analogous to that set out in Example (1b). 3.5 grams 1-n-butyl-3,5-diphenyl-pyrazol-4-acetic acid were obtained, representing a yield of 64%. The substance had a M.P. of 97°–98° C.

EXAMPLE 27

(a) 12.0 grams 3,3-bis-(p-chlorobenzoyl)-propionic acid ethyl ester, 3.9 grams phenylhydrazine and 2.7 grams glacial acetic acid were mixed and the mixture was heated in a nitrogen atmosphere to the boiling temperature under reflux for 6 hours. To the reaction mixture were than added benzene, and the pH was adjusted to 2–3, followed by extraction with water. The benzene was evaporated from the benzene phase and the dry, crystalline residue was recrystallized from a mixture of cyclohexane and petroleum ether boiling in a range from 50°–70° C. 13.0 grams 1-phenyl-3,5-bis-(p-chlorophenyl)-pyrazol-4-acetic acid ethyl ester, melting at 120°–122° C., were obtained, representing a yield of 91%.

The 3,3-bis-(p-chlorobenzoyl)-propionic acid-ethyl ester used in Example (27a) as the starting material was produced by a procedure analogous to that described in Example (2b) by the reaction of 1,3-bis-(p-chlorophenyl)-1,3-propaned one with bromoacetic acid-ethyl ester. The 3,3-bis-(p-chlorobenzoyl)-propionic acid-ethyl ester obtained in this manner has a M.P. of 108° C.

(b) 12.5 grams of the 1-phenyl-3,5-bis-(p-chlorophenyl)-pyrazol-4-acetic acid-ethyl ester produced in accordance with Example (27a) were saponified and the free acid recovered by a procedure analogous to that described in Example (1b). The saponification was completed as 1.5 hour of heating the reaction mixture to the boiling temperature. 8.9 grams 1-phenyl-3,5-bis(p-chlorophenyl)-pyrazol-4-acetic acid, melting at 204°–206° C., were obtained, representing a yield of 83%.

EXAMPLE 28

(a) 20 grams 1,3-bis-(m-methoxyphenyl)-1,3-propanedion were alkylated by reaction with a mixture of 3.4 grams of a 50% suspension of sodium hydride in paraffin oil and 12.9 grams bromoacetic acid ethyl ester in a procedure analogous to the procedure set out in Example (2b). The crude alkylation product obtained in this manner was reacted with 8.0 grams phenylhydrazine by a procedure analogous to that set out in Example (2c) to form the corresponding pyrazole ester, which was subsequently saponified by a procedure analogous to that described in Example 1b). 9.7 grams 1-phenyl-3,5-bis-(m-methoxyphenyl)-pyrazol-4-acetic acid, melting at 129°–131° C., were obtained, representing a yield of 33%.

(b) The 1,3-bis-(m-methoxy-phenyl)-1,3-propanedion used in Example (28a) as the starting material was produced by the reaction of m-methoxy-benzoic acid methylester, m-methoxy-acetophenone and sodium hydride in a procedure analogous to that described by Swamer and Hauser in J. Am. Chem. Soc. 72, 1352 (1950). The substance melted at 60°–71° C.

EXAMPLE 29

11.8 grams 3,3-dibenzoyl-propionic acid-ethyl ester, 5.5 grams cyclohexyl-hydrazine and 3.0 grams glacial acetic acid were mixed and the mixture was heated for 4 hours to 140° C. The reaction mixture was then worked up by a procedure analogous to the method set out in Example (2a) and the ester thus obtained was saponified and the free acid recovered by a procedure analogous to that described in Example (2b). 11.1 grams 1-cyclohexyl-3,5-diphenyl-pyrazol-4-acetic acid, melting at 229°–231° C., were obtained, representing a yield of 81%.

EXAMPLE 30

(a) 10 grams 4-dimethylamino-3-benzoyl-butene-(3)-acid-methylester and 4.7 grams phenylhydrazine were mixed and the mixture was heated for 4 hours to 100° C. The reaction mixture was taken up in benzene, the pH was adjusted to 3 to 4, followed by extraction with water. The benzene solution was then evaporated and the crude pyrazol acetic acid ester thus obtained was saponified in a mixture of 20 milliliters methanol and 25 milliliters 2n aqueous sodium hydroxide and the free acid recovered by a procedure analogous to that described in Example (1b). The free acid obtained in this manner was recrystallized from a mixture of benzene and petroleum ether, boiling in a range from 50°–70° C. 7.1 grams 1,5-diphenyl-pyrazol-4-acetic acid, melting at 107°–110° C., were obtained, representing a yield of 63%.

(b) The 4-dimethylamino-3-benzoyl-butene-(3)-acid-methylester used in Example (30a) as the starting material was produced as follows: 23 grams 3-benzoylpropionic acid-methylester, 30 grams dimethylformamidedimethyl-acetal and 1 gram glacial acetic acid were mixed and the mixture reacted for 8 hours in a bath heated to 120° C. Thereafter, the methanol, formed in the reaction, was distilled off in an additional 3 hours. The reaction mixture was thereafter evaporated in vacuo and the residue, thus obtained was recrystallized from a mixture of benzene and of petroleum ether boiling in a range from 50°–70° C. 14 grams 4-dimethylamino-3-benzoyl-butene-(3)-acid methylester, melting at 114°–115° C., were obtained.

EXAMPLE 31

5.5 grams 4-dimethylamino-3-benzoyl-butene-(3)-acid-methylester, 4.7 grams p-chlorophenylhydrazine-sulfate, 2.0 grams sodium acetate and 20 milliliters glacial acetic acid were mixed and the mixture was heated to the boiling temperature under reflux for 30 minutes. The reaction mixture thus obtained was worked up by a procedure analogous to that set out in Example (2a). The ester was saponified and the free acid was recovered by a procedure analogous to that described in Example (2b).

4.7 grams 5-phenyl-1-(p-chlorophenyl)-pyrazol-40acetic acid, melting at 110°–111° C., were obtained, representing a yield of 67%.

EXAMPLE 32

(a) 5 grams 4-dimethylamino-3-(p-chlorobenzoyl)-butene-(3)-acid-methylester, 2.0 grams phenylhydrazine and 1.0 gram glacial acetic acid were mixed and the mixture heated to 110° C. for 3 hours. The reaction mixture thus obtained was worked up by a procedure analogous to that set out in Example (2a). The ester was saponified and the free acid was recovered by a procedure analogous to that described in Example (2b). 4.1 grams 1-phenyl-5-(p-chlorophenyl)-pyrazol-4-acetic acid, melting at 185°–186° C., were obtained, representing a yield of 73%.

(b) 4-Dimethylamino-3-(p-chlorobenzoyl)-butene-(3)-acid-methylester used as the starting material in Example (32a) was obtained by reacting 3-(p-chlorobenzoyl)-acetal and recovering the reaction product by a procedure analogous to that described in Example (30b). The substance had a melting point of 100°–101° C.

EXAMPLE 33

4-Dimethylamino-3-(p-chlorobenzoyl)-butene-(3)-acid-methylester, p-chlorophenylhydrazine-sulfate, sodium acetate and glacial acetic acid were reacted and the reaction product recovered by a procedure analogous to that described in Example 31. 1,5-Bis-(p-chlorophenyl)-pyrazol-4-acetic acid, melting at 195°–196° C., was obtained in a yield of 60%.

EXAMPLE 34

10 grams diisovalerylmethane (as described by Swamer and Hauser), were reacted with 1.3 gram of a 50% suspension of sodium hydride in paraffin oil and 10 grams bromoacetic acid-ethylester by a procedure analogous to that described in Example (2b). The benzene solution obtained in this procedure was evaporated and the residue of crude 3,3-diisovalerylpropionic acid-ethyl ester obtained thereby was mixed with 6.5 grams phenylhydrazine and 4 grams glacial acetic acid and the mixture was heated to the boiling temperature under reflux for 2 hours. The reaction mixture obtained thereby was then worked up in accordance with a procedure analogous to that described in Example (1a). The ester thus recovered was saponified and the free acid recovered by a procedure analogous to that described in Example (1b). 7.5 grams 3,5-diisobutyl-1-phenyl-pyrazol-4-acetic acid, melting at 125°–126° C., were obtained representing a yield of 44% on the diisovalerylmethane starting material.

EXAMPLE 35

(a) 8 grams 1-cyclohexyl-3-(p-tolyl)-1,3-propanedion were reacted with 6.3 grams bromoacetic acid-ethyl ester and 1.6 grams of a 50% suspension of sodium hydride in a manner as described in Example 34. The crude alkylation product obtained thereby was further reacted with 3.8 grams phenylhydrazine in a manner similar to that described in Example 34 to form the corresponding pyrazol ester, which was, without further purification, saponified by alkali by a procedure analogous to that described in Example (1b). 9.1 grams 3-cyclohexyl-1-phenyl-5-(p-tolyl)-pyrazol-4-acetic acid, melting at 189°–191° C., were obtained, representing a yield of 74%.

(b) 1-cyclohexyl-3-(p-tolyl)-1,3-propanedione used in Example (35a) as the starting material was prepared by reacting 4-methylacetophenone, cyclohexane carbonic acid-methylester and sodium hydride and recovering the reaction product by a procedure analogous to that described by Swamer and Hauser in J. Am. Chem. Soc. 72, 1352 (1950). The new substance had a M.P. of 55°–56° C.

EXAMPLE 36

(a) 18 grams 2-methyl-3,3-diacetyl-propionic acid-ethyl ester, 10.5 grms phenylhydrazine and 6.5 grams glacial acetic acid were mixed and the mixture heated to the boiling temperature under reflux for 5 hours. The reaction mixture was worked up and saponified in accordance with a procedure analogous to that set out in Example (2a). 14.6 grams α-3,5-trimethyl-1-phenyl-pyrazol-4-acetic acid, melting at 129°–130° C., were obtained, representing a yield of 71%.

(b) 2-methyl-3,3-diacetyl-propionic acid-ethyl ester used as the starting material in Example (36a) was obtained by alkylation of acetylacetone with α-bromopropionic acid-ethyl ester and sodium hydride in dimethylformamide as the solvent by a procedure analogous to that described above. 2-methyl-3,3-diacetyl-propionic acid-ethyl ester, having a $Kp_{10}$ of 125°–130° C., was obtained in a yield of 59%.

EXAMPLE 37

20 grams 1,3-diphenyl-1,3-propanedion, 4.3 grams of a 50% suspension of sodium hydride in paraffin oil, 20 grams -bromopropionic acid-ethyl ester and 300 milliliters dimethylformamide were mixed and the mixture was stirred for 20 hours at room temperature and for another 20 hours at 50° C. The reaction mixture containing the 2-methyl-3,3-dibenzoyl-propionic acid-ethyl ester formed in the reaction was worked up in accordance with a procedure analogous to that set out in Example (2b). The crude product obtained thereby was further reacted with 9.0 grams phenylhydrazine and 8 grams glacial acetic acid in accordance with a procedure analogous to that described in Example (2c). The crude pyrazol ester obtained in this manner was saponified to form the free acid in a procedure analogous to that set above. 5.7 grams -methyl-1,3,5-triphenyl-pyrazol-4-acetic acid, melting at 95°–99° C. were obtained, corresponding to a yield of 17% based on the diketone starting material.

EXAMPLE 38

(a) 2.3 grams 3,5-dimethyl-1-phenyl-pyrazol-4-acetic acid were dissolved in the equivalent volume of aqueous sodium hydroxide and the solution was evaporated and to the dry residue were added acetone with stirring. By filtration, the sodium salt of 3,5-dimethyl-1-phenyl-pyrazol-4-acetic acid, melting at 216°–217° C., was recovered.

(b) Using 1,3,5-triphenyl-pyrazol-4-acetic acid as the starting material the sodium salt of this acid was obtained by a procedure analogous to that described in Example (38a). This salt melted at 209°–210° C.

EXAMPLE 39

To a concentrated solution of the sodium salt of the 3,5-dimethyl-1-phenyl-pyrazol-4-acetic acid was added concentrated calcium chloride solution. The precipitate formed thereby was filtered off, and washed first with concentrated calcium-chloride solution and thereafter with ice cold water. The calcium salt of the acid obtained in this manner melted at 285°–290° C. with decomposition.

EXAMPLE 40

To a solution of 3,5-dimethyl-1-phenyl-pyrazol-4-4-acetic acid in ether was added dropwise a small excess of morpholine. The morpholine salt of the acid precipitating thereby, was separated by filtration and had a melting point of 131°–132° C.

EXAMPLE 41

By the reaction of 3,3-dibenzoyl-propionic acid ethyl ester with the following substituted hydrazines or their salts:
p-fluorophenylhydrazine,
m-chlorophenylhydrazine, p-methoxyphenylhydrazine,
p-ethoxyphenylhydrazine
p-bromophenylhydrazine,
m-bromophenylhydrazine,
3,4-dichlorophenylhydrazine,
2,4-dichlorophenylhydrazine,
3-chloro-2-methylphenylhydrazine,
3,4-dimethylphenylhydrazine,
2,5-dimethylphenylhydrazine,
p-tolylhydrazine,
m-tolylhydrazine,
in accordance with a procedure similar to that set out in Example 21 the following substituted pyrazol-4-acetic acid derivatives are obtained over the corresponding pyrazol-4-acetic acid-ethyl ester:

3,5-diphenyl-1-(p-fluorophenyl)-pyrazol-4-acetic acid (M.P. 196°–197° C.,)
3,5-diphenyl-1-(m-chlorophenyl)-pyrazol-4-acetic acid,
3,5-diphenyl-1-(p-methoxyphenyl)-pyrazol-4-acetic acid (M.P. 195°–196° C.,),
3,5-diphenyl-1-(p-ethoxyphenyl)-pyrazol-4-acetic acid,
3,5-diphenyl-1-(p-bromophenyl)-pyrazol-4-acetic acid,
3,5-diphenyl-1-(m-bromophenyl)-pyrazol-4-acetic acid,
3,5-diphenyl-1-(3,4-dichlorophenyl)-pyrazol-4-acetic acid,
3,5-diphenyl-1-(2,4-dichlorophenyl)-pyrazol-4-acetic acid,
3,5-diphenyl-1-(3-chloro-2-methylphenyl)-pyrazol-4-acetic acid,
3,5-diphenyl-1-(3,4-dimethylphenyl)-pyrazol-4-acetic acid,
3,5-diphenyl-1-(2,5-dimethylphenyl)-pyrazol-4-acetic acid,
3,5-diphenyl-1-(p-tolyl)-pyrazol-4-acetic acid,
3,5-diphenyl-1-(m-tolyl)-pyrazol-4-acetic acid.

EXAMPLE 42

By a method analogous to that described in Example 24, 3,5-heptane was reacted with bromoacetic acid-ethyl ester to form 3,3-dipropionyl-propionic acid-ethyl ester, which was further reacted with phenylhydrazine to produce 3,5-diethyl-1-phenyl-pyrazol-4-acetic acid-ethyl ester which was saponified to form the free acid. Obtained was 3,5-diethyl-1-phenyl-pyrazol-4-acetic acid having a melting point of 129°–130° C.

EXAMPLE 43

By a method analogous to that described in Example 34 1-cyclohexyl-3-phenyl-1,3-propanedion was reacted to form 3-cyclohexanoyl-3-benzoyl-propionic acid ethyl ester, which was reacted with phenyl-hydrazine to form 3-cyclohexyl-1,5-diphenyl-pyrazol-4-acetic acid-ethyl ester and finally by saponification 3-cyclohexyl-1,5-diphenyl-pyrazol-4-acetic acid, having a melting point of 176°–178° C.

EXAMPLE 44

By a method analogous to that described in Example 28, 1-phenyl030(p-methoxyphenyl)-1,3-pripanedion was reacted with bromoacetic acid-ethyl ester to form 3-benzoyl-3-p-anisoyl-propionic acid-ethyl ester, which was further reacted with phenylhydrazine to form 1,3-diphenyl-5-(p-methoxyphenyl)-pyrazol-4-acetic acid-ethyl ester, from which was obtained by saponification 1,3-diphenyl-5-(p-methoxyphenyl)-pyrazol-4-acetic acid having a melting point of 160°–163° C.

EXAMPLE 45

(a) 18.6 grams 3,3-diacetyl-propionic acid-ethyl ester, 6.0 grams glacial acetic acid, 9.0 grams n-butylhydrazine and 50 milliliters ethanol were mixed and the mixture was heated to the boiling temperature under reflux for 2 hours. The solution was then evaporated and the residue was taken up in ether. The ether phase was extracted first with water and thereafter with aqueous sodium bicarbonate solution, the ether phase was dried with calcium chloride, the ether evaporated and the residue fractionated. 18.2 grams 3,5-dimethyl-1-n-butyl-pyrazol-4-acetic acid-ethyl ester, having a $Kp_{0.001}$ of 86°–87° C. were obtained, representing a yield of 76%.

The substitution for the n-butyl-hydrazine in the reaction of the foregoing example by the following hydrazines:
methylhydrazine,
isopropylhydrazine,
2-methyl-propylhydrazine,
cyclopentylhydrazine,
cyclohexylhydrazine, and
benzylhydrazine gives the following pyrazol-4-acetic acid ethyl ester in analogous manner:
1,3,5-trimethyl-pyrazol-4-acetic acid-ethyl ester,
3,5-dimethyl-1-isopropyl-pyrazol-4-acetic acid-ethyl ester,
3,5-dimethyl-1-isobutyl-pyrazol-4-acetic acid-ethyl ester,
3,5-dimethyl-1-cyclopentyl-pyrazol-4-acetic acid-ethyl ester,
3,5-dimethyl-1-cyclohexyl-pyrazol-4-acetic acid-ethyl ester, and
3,5-dimethyl-1-benzyl-pyrazol-4-acetic acid-ethyl ester.

(b) by saponification of the pyrazol-4-acetic acid-ethyl esters obtained in accordance with Example (45a), in accordance with the method analogous to that described in Example (3b), the following free acids are obtained:
3,5-dimethyl-1-n-butyl-pyrazol-4-acetic acid (M.P. 97°–98° C.),
1,3,5-trimethyl-pyrazol-4-acetic acid (M.P. 228°–230° C.),
3,5-dimethyl-1-isopropyl-pyrazol-4-acetic acid,
3,5-dimethyl-1-isobutyl-pyrazol-4-acetic acid,
3,5-dimethyl-1-cyclohexyl-pyrazol-4-acetic acid,
3,5-dimethyl-1-benzyl-pyrazol-4-acetic acid (M.P. 119121° C.).

EXAMPLE 46

(a) 10 grams acetylacetone were reacted with 5 grams of a 50% suspension of sodium hydride in paraffin oil and with 25 grams bromoacetic acid-benzylester in accordance with a procedure analogous to that set out in Example (2b). 3,3-diacetyl-propionic acid-benzylester having a $Kp_{0.005}$ of 126°–128° C. was obtained. This substance was further reacted with phenylhydrazine by a procedure analogous to that set out in Example (2c). 3,5-dimethyl-1-phenyl-pyrazol-4-acetic acid-benzylester, having a $Kp_{0.001}$ of 205°–209° C., was obtained in a yield of 51%.

(b) Saponification of the benzylester produced in Example (46a) by a procedure analogous to that set out in Example (1b) produced 3,5-dimethyl-1-phenylpyrazol-4-acetic acid, melting at 137°–139° C., in a yield of 88%.

(c) 2 grams of the pyrazol-4-acetic acid-benzyl ester produced by the method of Example (46a) were dissolved in 100 milliliters ethyl acetate and after addition of 5 milliliters glacial acetic acid hydrogenated for 5 hours at normal pressure and at room temperature on 5% palladium-carbon in a circulatory hydrogenator. The free acid was obtained in a yield of 92%.

EXAMPLE 47

(a) 6.0 grams 3-benzoyl-levulinic acid ethyl ester, 2.7 grams 2-hydrazino-pyridine and 25 milliliters glacial acetic acid were mixed and the mixture was heated to the boiling temperature under reflux for 3 hours. The reaction mixture was worked up by a procedure analogous to that described above. 5.0 grams 3-methyl-5-phenyl-1-(2-pyridyl)-pyrazol-4-acetic acid ethyl ester, melting at 89°–90° C., were obtained, representing a yield of 64%.

(b) The pyrazol-4-acetic acid ethyl ester produced by Example (47a) was subjected to alkaline saponification by a procedure analogous to that set out in Example (1b). 3-methyl-5-phenyl-1-(2-pyridyl)-pyrazol-4-acetic acid, melting at 182°–183° C. was obtained in a yield of 81%.

(c) The method of Example (47a) was repeated, with the substitution of 3-hydrazino-pyridine for the 2-hydrazino-pyridine used in Example (47a). 3-methyl-5-phenyl-1-(3-pyridyl)pyrazol-4-acetic acid-ethyl ester was obtained, which was subsequently saponified by a method analogous to that described in Example (47b) to produce 3-methyl-5-phenyl-1-(3-pyridyl)-pyrazol-4-acetic acid melting at 197°–199° C.

EXAMPLE 48

Following a procedure analogous to that described in Example 26, 3,5-diphenyl-1H-pyrazol-4-acetic acid-ethyl ester is reacted, instead with n-butylbromide as described in Example 26, with the following compounds:
methyliodide,
ethylbromide,
benzylchloride,
p-chlorobenzylchloride,
m-chlorobenzylchloride,
p-bromobenzylbromide,
o-fluorobenzylchloride,
p-fluorobenzylbromide or p-methoxybenzylchloride After saponification of the reaction product by a method analogous to that used in Example 26, the following compounds are obtained:
1-methyl-3,5-diphenyl-pyrazol-4-acetic acid (M.P. 170°–172° C.),
1-ethyl-3,5-diphyl-pyrazol-4-acetic acid,
3,5-diphenyl-1-benzyl-pyrazol-4-acetic acid,
3,5-diphenyl-1-(p-chlorobenzyl)-pyrazol-4-acetic acid,
3,5-diphenyl-1-(m-chlorobenzyl)-pyrazol-4-acetic acid,
3,5-diphenyl-1-(p-bromobenzyl)-pyrazol-4-acetic acid,
3,5-diphenyl-1-(o-fluorobenzyl)-pyrazol-4-acetic acid,
3,5-diphenyl-1-(p-fluorobenzyl)-pyrazol-4-acetic acid, and
3,5-diphenyl-1-(p-methoxybenzyl)-pyrazol-4-acetic acid.

EXAMPLE 49

Following a procedure analogous to that described in Example (2b), 1,3-di-(2-thienyl)-1,3-propanedione was alkylated by reaction with bromoacetic acid ethyl ester to form 3,3-di-(2-thienoyl)-propionic acid ethyl ester, which was reacted with phenylhydrazine in accordance with a procedure analogous to that set out in Example (2c) to form 1-phenyl-3,5-di-(2-thienyl)-pyrazol-4-acetic acid ethyl ester. This substance was saponified by a procedure analogous to that described in Example (1b). 1-Phenyl-3,5-di-(2-thienyl)-pyrazol-4-acetic acid, melting at 216°–218° C., was obtained in a yield of 56% based on the propanedione starting material.

EXAMPLE 50

(a) Following a procedure analogous to that described in Example 49, 1,3-di-(2-furyl)-1,3-propanedion was alkylated to form 3,3-di-(2-furoyl)-propionic acid-ethyl ester, which was further reacted with phenylhydrazine to produce 1-phenyl-3,5-di-(2-furyl)-pyrazol-4-acetic acid-ethyl ester, which by saponification result in the free acid. 1-phenyl-3,5-di-(2-furyl)-pyrazol-4-acetic acid, melting at 199°–202° C., was obtained in a yield of 48% based on the 1,3-di-(2-furyl)-1,3-propanedione starting material.

(b) The procedure of Example (50a) is repeated with the substitution of p-chlorophenyl-hydrazine for phenyl-hydrazine. 1-(p-chlorophenyl)-3,5-di-(2-furyl)-pyrazol-4-acetic acid is obtained.

EXAMPLE 51

Following a procedure analogous to that set out in Example 49, 40 grams 1-phenyl-3-(2-furyl)-1,3-propanedione were alkylated by reaction with 36 grams bromoacetic acid-ethyl ester and 23 grams of a 20% suspension of sodium hydride in paraffin oil to form 3-benzoyl-3-(2-furoyl)-propionic acid-ethyl ester, which was further reacted with 28 grams phenylhydrazine in glacial acetic acid to form the respective pyrazol-4-acetic acid-ethyl esters, which without being separated, were saponified in accordance with a procedure analogous to that described in Example (1b).

43 grams of a mixture of about 1 part by weight 1,3-diphenyl-5-(2-furyl)-pyrazol-4-acetic acid having a melting point of 183.5°–194.5° C. and about 3 parts by weight 1,5-diphenyl-3-(2-furyl)-pyrazol-4-acetic acid were obtained. The mixture of the two compounds in the approximate 3:1 ratio, as obtained in the method, melted at 166°–174° C.

EXAMPLE 52

8.7 grams 3,3-dibenzoyl-propionic acid ethyl ester, 5.0 grams 3-hydrazino-pyridine and 6.0 grams glacial acetic acid were mixed and the mixture heated to the boiling temperature under reflux for 5 hours. The reaction product was further processed by a procedure analogous to that described in Example (2a). 6.1 grams 3,5-diphenyl-1-(3-pyridyl)-pyrazol-4-acetic acid, melting at 185°–187° C., were obtained, representing a yield of 62%.

EXAMPLE 53

(a) 17.6 grams 1-phenyl-3-(p-chlorophenyl)-pyrazol-4-acetonitrile and 180 milliliters 25% aqueous hydrochloric acid were mixed and heated to the boiling temperature under reflux for 6 hours. To the mixture was then added dropwise concentrated aqueous sodium hydroxide until the pH of the mixture reached a value in the range from 3 to 5. The free pyrazol-4-acetic acid precipitated thereby are filtered off, redissolved in dilute aqueous sodium hydroxide, the solution cleared by treatment with activated carbon, and the pyrazol-4-acetic acid precipitated by acidifying the solution by the addition of dilute mineral acid, sulfuric acid. The filtered acid was crystallized from a mixture of ethanol and water. 17.1 grams 1-phenyl-3-(p-chlorophenyl)-pyrazol-4-acetic acid, melting at 148°–150° C., were obtained, representing a yield of 91%.

(b) Following the procedure set out in Example (53a), and starting from the corresponding substituted pyrazol-4-acetonitriles described in Example (54b) the following substituted pyrazol-4-acetic acids are obtained:

1,3-diphenyl-pyrazol-4-acetic acid (M.P. 275°–277° C.),
1,3,5-triphenyl-pyrazol-4-acetic acid (M.P. 221°–212° C.),
1-phenyl-3-(p-fluorophenyl)-pyrazol-4-acetic acid (M.P. 151°–152° C.),
1-phenyl-3-(p-bromophenyl)-pyrazol-4-acetic acid (M.P. 141°–142° C.),
1-phenyl-3-(p-methoxyphenyl)-pyrazol-4-acetic acid (M.P. 160°–162°.),
1-phenyl-3-(p-butoxyphenyl)-pyrazol-4-acetic acid,
1-phenyl-3-(3,4-dimethoxyphenyl)-pyrazol-4-acid,
3-(p-chlorophenyl)-1-(p-methoxyphenyl)-pyrazol-4-acetic acid (M.P. 141°–142.4° C.),
1-phenyl-3-(p-methylmercaptophenyl)-pyrazol-4-acetic acid
3-(p-chlorophenyl)-1-(p-tolyl)-pyrazol-4-acetic acid,
3-phenyl-1-(p-fluorophenyl)-pyrazol-4-acetic acid (M.P. 126°–128° C.).
3-phenyl-1-(p-chlorophenyl)-pyrazol-4-acetic acid (M.P. 161°–162° C.).
1-phenyl-3-(3-pyridyl)-pyrazol-4-acetic acid (M.P. 217°–219° C.).
1-(p-chlorophenyl)-3-(2-furyl)-pyrazol-4-acetic acid,
3-methyl-1-(p-chlorophenyl)-pyrazol-4-acetic acid,
1-phenyl-3-(m-tolyl)-pyrazol-4-acetic acid,
1-phenyl-3-(p-tolyl)-pyrazol-4-acetic acid,
1-phenyl-3-(α,α,α-trifluoro-m-tolyl)-pyrazol-4-acetic acid,
3-phenyl-1-(2-naphthyl)-pyrazol-4-acetic acid,
1-phenyl-3-(1-naphthyl)-pyrazol-4-acetic acid,
1-phenyl-3-(2-naphthyl)-pyrazol-4-acetic acid (M.P. 176°–176.5° C.),
1-phenyl-3-(5-indanyl)-pyrazol-4-acetic acid,
1-phenyl-3-(6-tetralyl)-pyrazol-4-acetic acid,
1-phenyl-3-(3,4-methylene-dioxyphenyl)-pyrazol-4-acetic acid,
1-phenyl-3-(p-cyclohexylphenyl)-pyrazol-4-acetic acid,
1-phenyl-3-(3,4-dimethyl-phenyl)-pyrazol-4-acetic acid,

EXAMPLE 54

(a) A hot solution of 40 grams 4-hydroxy-methyl-1-phenyl-3-(p-chlorophenyl)-pyrazol in 500 milliliters benzene was added dropwise during 2 hours to 167 grams boiling temperature under reflux for another 3 hours. (In an alternate method the components were mixed cold and thereafter heated to the boiling temperature under reflux for 6 hours.) The solution, thus obtained, was evaporated in vacuo, 250 milliliters benzene were added to the residue and the benzene again evaporated. The residue, consisting of crude 4-chloromethyl-1-phenyl-3-(p-chlorophenyl)-pyrazol, was slowly, over a time period of 50 minutes, given into a solute of 34 grams sodium cyanide in 300 milliliters dimethyl-sulfoxide at 40° C. and thereafter stirred at 40° C. for one more hour and left at room temperature over night. To the mixture were thereafter added 900 milliliters chloroform.

The mixture was then several times extracted with water and the separated organic phase was dried with anhydrous sodium sulfate. The solution was evaporated, leaving 42 grams of a solid residue, which was recrystallized from a mixture of benzene and petroleum ether boiling. 38 grams 1-phenyl-3-(p-chlorophenyl)-pyrazol-4-acetonitrile, melting at 124°–124.5° C., were obtained, representing a yield of 92%.

(b) Repeating the method of Example (54a), however, substituting the correspondingly substituted 4-hydroxymethyl-pyrazoles, the following acetonitrile compounds were obtained over the corresponding chloromethyl-pyrazoles;

3,5-dimethyl-1-phenyl-pyrazol-4-acetronitrile (M.P. 69°–70° C.),
1,3-diphenyl-pyrazol-4-acetonitrile (M.P. 88°–89° C.),
1,3,5-triphenyl-pyrazol-4-acetonitrile (M.P. 123.5°–124° C.),
1-phenyl-3-(p-fluorophenyl)-pyrazol-4-acetonitrile (M.P. 119°–120° C.),
1-phenyl-3-(p-bromophenyl)-pyrazol-4-acetonitrile (M.P. 134°–136° C.)
1-phenyl-3-(p-methoxyphenyl)-pyrazol-4-acetonitrile (M.P. 123°–24° C.)
1-phenyl-3-(p-butoxyphenyl)-pyrazol-4-acetonitrile
1-phenyl-3-(3,4-dimethoxyphenyl)-pyrazol-4-acetonitile
3-(p-chlorophenyl)-1-(p-methoxyphenyl)-pyrazol-4-acetonitrile (M.P. 131°–132° C.)
1-phenyl-3-(p-methoxymercaptophenyl)-pyrazol-4-acetonitrile
3-(p-chlorophenyl)-1-(p-tolyl)-pyrazol-4-acetonitrile
3-phenyl-1-(p-fluorophenyl)-pyrazol-4-acetonitrile (M.P. 118°–119° C.)
3-phenyl-1-(p-chlorophenyl)-pyrazol-4-acetonitrile (M.P. 99°–100° C.)
3-phenyl-1-(p-bromohenyl)-pyrazol-4-acetonitrile (M.P. 85°–87° C.)
1-phenyl-3-(3-pyridyl)-pyrazol-4-acetonitrile (M.P. 133°–135° C.)
1-(p-chlorophenyl)-3-(2-furyl)-pyrazol-4-acetonitrile
3-methyl-1-(chlorophenyl)-pyrazol-4-acetonitrile
1-phenyl-3-(m-tolyl)-pyrazol-4-acetonitrile
1-phenyl-3-(p-tolyl)-pyrazol-4-acetonitrile
1-phenyl-3-(α,α,α-trifluoro-m-tolyl)-pyrazol-4-acetonitrile
3-phenyl-1-(2-naphthyl)-pyrazol-4-acetonitrile
1-phenyl-3-(1-naphthyl)-pyrazol-4-acetonitrile
1-phenyl-3-(2-naphthyl)-pyrazol-4-acetonitrile (M.P. 149.5°–150° C.)
1-phenyl-3-(5-indanyl)-pyrazol-4-acetonitrile
1-phenyl-3-(6-tetralyl)-pyrazol-4-acetonitrile
1-phenyl-3-(3,4-methylenedioxyphenyl)-pyrazol-4-acetonitrile
1-phenyl-3-(p-cyclohexylphenyl)-pyrazol-4-acetonitrile
1-phenyl-3-(3,4-dimethylphenyl)pyrazol-4-acetonitrile (c) The 4-hydroxymethylpyrazoles, used as the starting material in Example (54b) are produced in the manner described hereinafter.

(d) 138 grams phosphorus oxychloride were slowly added drop by drop at 5°–10° C. to 263 grams dimethylformamide followed by stirring for 1 hour without further cooling. Thereafter 100 grams p-chloro-acetophenone-phenylhydrazene were added at 15°–20° C. to the mixture which was then heated to 70° C. for 6 hours. If a difficulty stirrable precipitate forms, the mixture is further diluted by the addition of 300–400 milliliters dimethylformamide. The reaction mixture was then stirred into 500 grams ice in 500 milliliters water, the pH adjusted to 7 by the dropwise addition of concentrated aqueous sodium hydroxide solution followed by another 5 hours stirring of the reaction mixture. The precipitate, consisting of the aldehyde formed in the reaction, was then filtered off by suction and washed with water. The precipitate was thereafter incorporated into aqueous sodium bicarbonate solution and the mixture was heated to the boiling temperature for about 1 hour. 114 grams 1-phenyl-3-(p-chlorophenyl)-pyrazol-4-aldehyde, melting at 140°–141° C., were obtained, representing a yield of 99%.

(e) The procedure described in the foregoing Example (54d) was modified, by omitting the direct hydrolysis with a mixture of ice and water. Instead, the reaction mixture was diluted by the addition of 500 milliliters methanol, and by the addition of a solution of 65 grams sodium perchlorate-monohydrate in methanol, [[1-phenyl-3-(p-chlorophenyl)-pyrazol-4-yl]-methylene]-dimethylammonium perchlorate, having a melting point of 256°–258° C., was nearly quantitatively precipitated. This product was thereafter subjected to alkaline hydrolysis in a manner similar to that described in Example (54d) to produce the 1-phenyl-3-(p-chlorophenyl)-pyrazol-4-aldehyde.

(f) Using the method of Examples (54d) or (54e) and substituting therein for the p-chloro-acetophenonephenyl-hydrazone starting material the arylhydrazones of the correspondingly substituted methylketones, the following pyrazol-4-aldehydes are obtained:

1,3-diphenyl-pyrazol-4-aldehyde (M.P. 143°–144° C.)
1-phenyl-3-(p-fluorophenyl)-pyrazol-4-aldehyde (M.P. 161.5°–162.5° C.)
1-phenyl-3-p-bromophenyl)-pyrazol-4-aldehyde (M.P. 144°–145° C.)
1-phenyl-3-(p-methoxyphenyl)-pyrazol-4-aldehyde (M.P. 137.5°–138.5° C.)
1-phenyl-3-(p-butoxyphenyl)-pyrazol-4-aldehyde
1-phenyl-3-(3,4-dimethoxyphenyl)-pyrazol-4-aldehyde
3-(p-chlorophenyl)-1-(p-methoxyphenyl)-pyrazol-4-aldehyde (M.P. 148°–149° C.)
1-phenyl-3-(p-methylmercaptophenyl)-pyrazol-4-aldehyde
3-phenyl-1-(p-fluorophenyl)-pyrazol-4-aldehyde (M.P. 171°–173° C.)
3-phenyl-1-(p-chlorophenyl)-pyrazol-4-aldehyde (M.P. 149°–150° C.)
3-phenyl-1-(p-bromophenyl)-pyrazol-4-aldehyde (M.P. 153.5°–154.5° C.)
1-phenyl-3-(3-pyridyl)-pyrazol-4-aldehyde (M.P. 157°–158° C.)
1-(p-chlorophenyl)-3-(2-furyl)-pyrazol-4-aldehyde (M.P. 160°–160.5° C.)
3-methyl-1-(p-chlorophenyl)-pyrazol-4-aldehyde
1-phenyl-3-(m-tolyl)-pyrazol-4-aldehyde
1-phenyl-3-(p-tolyl)-pyrazol-4-aldehyde
1-phenyl-3-($\alpha$, $\alpha,\alpha$-trifluoro-m-tolyl)-pyrazol-4-aldehyde
3-phenyl-1-(2-naphthyl)-pyrazol-4-aldehyde
1-phenyl-3-(1-naphthyl)-pyrazol-4-aldehyde
1-phenyl-3-(2-naphthyl)-pyrazol-4-aldehyde (M.P. 143.5°–145° C.)
1-phenyl-3-(5-indanyl)-pyrazol-4-aldehyde
1-phenyl-3-(6-tetralyl)-pyrazol-4-aldehyde
1-phenyl-3-(3,4-methylenedioxyphenyl)-pyrazol-4-aldehyde
1-phenyl-3-(p-cyclohexylphenyl)-pyrazol-4-aldehyde
1-phenyl-3-(3,4-dimethylphenyl)-pyrazol-4-aldehyde (g) 32 grams phosphorus oxychloride were added dropwise at 0°–5° C. to 75 grams dimethylformamide. The mixture was thereafter stirred for 1 hours at room temperature. Thereafter, 25 grams 1,3,5-triphenyl-pyrazol were added to the mixture, which was then stirred for 8 hours at 80° C. The reaction mixture, was evaporated and water added to the residue. The pH of the aqueous mixture was adjusted to 8–10. The precipitate was separated and crystallized from ethanol. 22 grams 1,3,5-triphenyl-pyrazol-4-aldehyde, melting at 159°–160° C., were obtained, representing a yield of 80%.

(h) The method, described in Example (54g) was repeated, substituting for the 1,3,5-triphenyl-pyrazol starting material 3,5-dimethyl-1-phenyl-pyrazol. 1,3-dimethyl-1-phenyl-pyrazol-4-aldehyde, melting at 122°–124° C., was obtained.

(i) 80 grams 1-phenyl-3-(p-chlorophenyl)-pyrazol-4-aldehyde were dissolved in a mixture of 800 milliliters ethanol and 1200 milliliters dimethylformamide. To the solution thus obtained, 5.5 grams 95% sodium borohydride were added in small portions at 20°–25° C. The mixture was then stirred for one more hour at room temperature. Thereafter, the reaction mixture was evaporated and the residue was taken up, with rubbing, with ethanol and water were thereafter added. The precipitate formed thereby was separated, dispersed and stirred in warm water, the precipitate was filtered off by suction, dried and recrystallized from benzene. 75 grams 4-hydroxymethyl-1-phenyl-3-(p-chloropheny)-pyrazol, melting at 141°–142° C., were obtained, representing a yield of 93%.

(j) Following the general procedure set out in Example 54i), but substituting as the starting material the correspondingly substituted pyrazol-4-aldehydes, the following 4-hydroxymethyl-pyrazols are obtained:

3,5-dimethyl-4-hydroxymethyl-1-phenyl-pyrazol
4-hydroxymethyl-1,3-diphenyl-pyrazol (M.P. 101°–103° C.)
4-hydroxymethyl-1,3,5-triphenyl-pyrazol (M.P. 143°–144° C.)
4-hydroxymethyl-1-phenyl-3-(p-fluorophenyl)-pyrazol (M.P. 118119° C.)
4-hydroxymethyl-1-phenyl-3-(p-bromophenyl)-pyrazol (M.P. 156°–157° C.)
4-hydroxymethyl-1-phenyl-3-(p-methoxyphenyl)-pyrazol (M.P. 127°–128° C.)
4-hydroxymethyl-1-phenyl-3-(p-butoxyphenyl)-pyrazol
4-hydroxymethyl-1-phenyl-3-(3,4-dimethoxyphenyl)-pyrazol
4-hydroxymethyl-3-(p-chlorophenyl)-1-(p-methoxyphenyl)-pyrazol (M.P. 128°–129° C.)
4-hydroxymethyl-1-phenyl-1-(p-fluorophenyl)-pyrazol (M.P. 135°–137° C.)
4-hydroxymethyl-3-phenyl-1-(p-chlorophenyl)-pyrazol (M.P. 132°–133° C.)

4-hydroxymethyl-3-phenyl-1-(p-bromophenyl)-pyrazol (M.P. 137°–138° C.)
4-hydroxymethyl-1-phenyl-3-(3-pyridyl)-pyrazol (M.P. 133°–134° C.)
4-hydroxymethyl-1-(p-chlorophenyl)-3-(3-furyl)-pyrazol (M.P. 120.5°–122° C.)
3-methyl-4-hydroxymethyl-1-(p-chlorophenyl)-pyrazol
4-hydroxymethyl01-phenyl-(m-tolyl)-pyrazol
4-hydroxymethyl-1-phenyl-3-(p-tolyl)-pyrazol
4-hydroxymethyl-1-phenyl-3-($\alpha,\alpha,\alpha$-trifluoro-m-tolyl)-pyrazol
4-hydroxymethyl-3-phenyl-1-(2-naphthyl)-pyrazol
4-hydroxymethyl-1-phenyl-3-(1-naphthyl)-pyrazol
4-hydroxymethyl-1-phenyl-3-(2-naphthyl)-pyrazol M.P. 157°–158° C.)
4-hydroxymethyl-1-phenyl-3-(5-indanyl)-pyrazol
4-hydroxymethyl-1-phenyl-3-(6-tetralyl)-pyrazol
4-hydroxymethyl-1-phenyl-3-(3,4-methylenedioxyphenyl)-pyrazol
4-hydroxymethyl-1-phenyl-3-(p-cyclohexylphenyl)-pyrazol
4-hydroxymethyl-1-phenyl-3-(3,4-dimethylphenyl)-pyrazol

EXAMPLE 55

(a) 15 grams 1,3,5-triphenyl-pyrazol-4-acetic acid, 50 milliliters methanol, 40 milliliters carbon tetrachloride and 0.64 gram concentrated sulfuric acid were mixed and the mixture heated to the boiling temperature under reflux for 11 hours. The cooled reaction mixture was then extracted, first with sodium carbonate solution and thereafter with water. The organic phase was then dried and evaporated. The residue was recrystallized from a mixture of methanol and water. 14.2 grams 1,3,5-triphenylpyrazol-4-acetic acid-methyl ester, melting at 80.5°–81.5° C., were obtained, representing a yield of 91%.

(b) The method, described in Example (55a), was repeated substituting the respective substituted free pyrazol-acetic acids. The following substances were obtained: 3,5-dimethyl-1-phenyl-4-acetic acid-methyl ester (M.P. 63°–64° C.)
  1-phenyl-3-(p-chlorophenyl)-pyrazol-4-acetic acid-methylester and
  1-phenyl-3,5-di-(2-furyl)-pyrazol-4-acetic acid-methylester (M.P. 82.5°–84.5° C.)

EXAMPLE 56

7.0 grams 1,3,5-triphenyl-pyrazol-4-acetic acid, 3.1 grams phosphorus oxychloride and 40 milliliters benzene were mixed and the mixture was heated to the boiling temperature under reflux for 2 hours. The reaction mixture was then poured on ice, the pH adjusted to 6 by the addition of dilute aqueous sodium carbonate solution. The benzene solution was separated, washed with water, dried over anhydrous magnesium sulfate, and evaporated. The residue, consisting of 1,3,5-triphenyl-pyrazol-4-acetylchloride was taken up in 40 milliliters absolute ether. The ether solution was then added dropwise at 0°–3° C. and within 20 minutes to a solution of 2.8 grams salicyclic acid in a mixture of 20 milliliters ether and 4.2 grams pyridine. The mixture was after stirred for 25 minutes and thereafter pored on a mixture of ice and concentrated aqueous hydrochloric acid. The acid solution was separated, extracted with water, and the ether evaporated. The residue was recrystallized from ethanol. 5.1 grams 1,3,5-triphenyl-pyrazol-4-acetic acid-(2-carboxyphenyl)-ester, melting at 190°–191° C., were obtained representing a yield of 54%. In similar manner are obtained
  1,3,5-triphenyl-pyrazol-4-acetic acid-phenylester
  1,3,5-triphenyl-pyrazol-4-acetic acid n-butylester ($Kp_{0.001}$ 218°–220° C.)
  1-phenyl-3-(p-chlorophenyl)-pyrazol-4-acetic acid-isopropylester

EXAMPLE 57

A benzene solution of 1-phenyl-3-(p-chlorophenyl)-pyrazol-4-acetyl-chloride was prepared by a procedure analogous to that described in Example 56. The benzene solution of the acetylchloride was added dropwise at 0° C. to a solution of excess piperidine in absolute benzene. The pH of the reaction mixture was adjusted to 8–10 and thereafter the reaction mixture was worked up by a procedure analogous to that described above. 1-[$\alpha$-[1-phenyl-3-(p-chlorophenyl)-pyrazol-4-yl]-acetyl]-piperidine, melting at 125°–126° C., was obtained in a yield of 85%.

In similar manner there are obtained by the foregoing procedure:
  N,N-diethyl-1-phenyl-3-(p-chlorophenyl)-pyrazol-4-acetamide, M.P. 94°–95° C.,
  N,N-dimethyl-1,3,5-triphenyl-pyrazol-4-acetamide
  1-[-(1,3,5-triphenyl-pyrazol-4-yl)-acetyl]-piperidine,
  3,5-dimethyl-N,N-diethyl-1-phenyl-pyrazol-4-acetamide,
  N-[2-(1-phenyl-3-(p-chlorophenyl)-pyrazol-4-yl)-acetyl] morpholine, and
  N-[2-(1-phenyl-3-(p-chlorophenyl)-pyrazole-4-yl)-acetyl] pyrrolidine

EXAMPLE 58

3.54 grams 1,3,5-triphenyl-pyrazol-4-acetic acid, 1.68 gram phosphorus oxychloride and 30 milliliters benzene were mixed and the mixture heated to the boiling temperature under reflux for 2 hours. The reaction mixture, containing in benzene solution the correspondingly substituted acetyl chloride was then added dropwise at 0° C. to 30 milliliters 25% aqueous ammonia solution. The mixture was permitted to stand over night at room temperature. Thereafter, 30 milliliteres water and enough ethylacetate were added to cause dissolution of the crystalline mass formed in the reaction mixture. The organic phase was separated, dried with magnesium sulfate, evaporated and the residue was recrystallized from a mixture of ethanol and water. 3.2 grams 1,3,5-triphenyl-pyrazol-4-acetamide, melting at 207°–207.5° C., were obtained, representing a yield of 91%.

The following substances are produced in similar manner from the correspondingly substituted pyrazol-4-acetic acids:
  3,5-dimethyl-1-phenyl-pyrazol-4-acetamide (M.P. 169°–170° C.)
  3-cyclohexyl-1,5-diphenyl-pyrazol-4-acetamide (M.P. 197°–198° C.)
  N-ethyl-1,3,5-triphenyl-pyrazol-4-acetamide
  1-phenyl-3,5-di-(2-furyl)-pyrazol-4-acetamide

EXAMPLE 59

10 grams 3,5-dimethyl-1-phenyl-pyrazol-4-acetonitrile were added to 40 milliliters concentrated sulfuric acid and the mixture was stirred over night at room temperature. The reaction mixture was poured into a mixture of ice and water and the pH was adjusted to 8 by the addition of aqueous sodium hydroxide. 6.8 grams 3,5-dimethyl-1-phenyl-pyrazol-4-acetamide, melting at 169°-170° C., were obtained, representing a yield of 63%.

Following the same procedure there are produced the following:
1,3,5-triphenyl-pyrazol-4-acetonitrile
1-phenyl-3-(p-chlorophenyl)-pyrazol-4-acetonitrile
1-phenyl-3-(2-naphthyl)-pyrazol-4-acetonitrile
1,3,5-triphenyl-pyrazol-4-acetamide (M.P. 207°-207.5° C.)
1-phenyl-3-(p-chlorophenyl)-pyrazol-4-acetamide (M.P. 181.5°-182.5° C.), and
1-phenyl-3-(2-naphthyl)-pyrazol-4-acetamide

EXAMPLE 60

6 grams 3,5-dimethyl-1-phenyl-pyrazol-4-acetic acid-methyl-ester and 80 milliliters ammonia solution in methanol were mixed and the mixture heated in an autoclave to 160° C. for 6 hours. The reaction mixture was evaporated to dryness. 4.6 grams 3,5-dimethyl-1-phenyl-pyrazol-4-acetamide, melting at 160°-170° C., were obtained, representing a yield of 81%.

In analogous manner was produced from 1,3,5-triphenyl-pyrazol-4-acetic acid-methyl ester as the starting material 1,3,5-triphenyl-pyrazol-4-acetamide melting at 207°-207.5° C. and from 1-phenyl-3-(p-chlorophenyl)-pyrazol-4-acetic acid-ethyl ester as the starting material 1-phenyl-3-(p-chlorophenyl)-pyrazol-4-acetamide melting at 181.5°-182.5° C.

EXAMPLE 61

6 grams 3,5-dimethyl-1-phenyl-pyrazol-4-acetamide, 2.5 grams phosphorus-oxychloride and 9 milliliters dichloroethane were mixed and stirred for 2 hours at 100° C.) The reaction mixture was poured on ice, diluted by the addition of chloroform and neutralized by the addition of aqueous sodium hydroxide. The organic phase was separated, washed with water, dried and the solvent evaporated. 3,5-Dimethyl-1-phenyl-pyrazol-4-acetonitrile, melting at 69°-70° C., was obtained in a yield of 82%.

In a similar manner there was produced from 1,3,5-triphenyl-pyrazol-4-acetamide as the starting material, 1,3,5-triphenyl-pyrazol-4-acetonitrile, which had a melting point of 123°,124° C.

EXAMPLE 62

11.5 grams 3,5-dimethyl-1-phenyl-pyrazol-4-acetonitrile, 2.2 grams absolute ethanol and 150 milliliters absolute ether were mixed and the mixture was saturated at 0° C. with HCl-gas and permitted to stand for one week. The imide acid ester hydrochloride formed thereby was separated, dissolved in water, neutralized and heated for 30 minutes in a water bath. 3,5-Dimethyl-1-phenyl-pyrazol-4-acetic acid ethyl ester, having a melting point of 86°-87° C., was obtained.

EXAMPLE 63

4.2 grams 3,5-dimethyl-1-phenyl-pyrazol-4-acetonitrile, 50 milliliters ethanol, 1 milliliter water and 10 milliliters concentrated sulfuric acid were mixed and the mixture heated to the boiling temperature under reflux for 15 hours. The reaction mixture was poured onto ice water, and the pH adjusted to 8 by the addition of aqueous sodium carbonate solution. The mixture was then extracted with ether, the ether evaporated from the ether phase and the residue recrystallized from a mixture of ethanol and water.

3,5-Dimethyl-1-phenyl-pyrazol-4-acetic acidethyl ester, melting at 86°-87° C., was obtained.

EXAMPLE 64

5.0 grams 1-phenyl-3-(p-chlorophenyl)-pyrazol-4-acetic acid, 2.5 grams phosphorus oxychloride and 70 milliliters benzene were mixed and the mixture heated to the boiling temperature under reflux for 2 hours. The reaction mixture was poured on ice, the pH was adjusted to 6 by addition of aqueous sodium carbonate solution. The benzene solution was separated, washed with ice water and dried with anyhydrous magnesium sulfate. 4.45 grams hydroxylamine hydrochloride were dissolved in 14 milliliters absolute pyridine. To this solution was added at 0° C. a solution of 1.47 grams sodium in 28 milliliters absolute ethanol. The benzene solution of 1-phenyl-3-(p-chlorophenyl)-pyrazol-4-acetyl chloride produced in the first part of the experiment was then added drop by drop during 20 minutes and at 0° C. to the above mixture. After stirring for two hours, the reaction mixture was permitted to stand over night at room temperature. The reaction mixture was thereafter poured onto a mixture of ice and concentrated aqueous hydrochloric acid. The pH was adjusted to 3 and the precipitate formed thereby was filtered off by suction. The precipitate was recrystallized from a mixture of ethanol and water. 3.0 grams 1-phenyl-3-(p-chlorophenyl)-pyrazol-4-acethydroxamic acid, melting at 168°-169° C. with decomposition, were obtained, representing a yield of 55%.

Likewise, there was produced from 1,3,5-triphenyl-pyrazol-4-acetic acid as the starting material, 1,3,5-triphenyl-pyrazol-4-acethydroxamic acid, which melted at 97°-103° C., with decomposition.

The compounds of the invention falling under general Formula I and the pharmacologically acceptable salts thereof are valuable medicaments, which are distinguished by pronounced antiphlogistic (anti-inflammatory), analgesic and antipyretic effectiveness. The compounds of the invention are especially noteworthy for their anti-inflammatory effect and their broader theurspeutic index compared to other comparable anti-inflammatory agent, like indomethacin.

Of the compounds of Formula I, those wherein A is COOH are especially noteworthy for their anti-inflammatory and/or analgetic and/or temperature controlling properties.

Of the compounds of Formula I those wherein A is $COOR_5$, $CONR_6R_7$ and CN are especially noteworthy for their analgesic properties and these will be used preferentially when the anti-inflammatory effect is of secondary importance in the treatment desired, with the analgesic properties playing the primary role.

In view of the lack of anti-inflammatory activities of numerous substituted indole acetic and propionic acids (as reported in J., Am., Chem., Soc., 85, 488, (1963) it was unexpected to find that the new compounds of the general Formula I and their salts are distinguished by pronounced antiphlogistic, analgetic and antipyretic effectiveness coupled with a low toxicity.

The following further description and data of the representative examples of the compounds of the invention is typical and representative of the genus represented by Formula I.

In the following Tables I and II there are presented data for the toxicity of the selected compounds A to R and for the therapeutic effectiveness as compared to the respective effectiveness of the various known standard compounds. The tables show, that the new compounds of the invention are superior to the comparable known compounds by their more pronounced antiphlogistic and analgesic effectiveness and by their greater therapeutic breadth.

The following representative compounds of the invention are compared in the Tables I and II, with phenylbutazone and indomethacin and with aminophenazone, respectively.

(A) 1,3,5-triphenyl-pyrazol-4-acetic acid
(B) 1-phenyl-3,5-di-(2-furyl)-pyrazol-4-acetic acid
(C) 3,5-diphenyl-1-(3-pyridyl)-pyrazol-4-acetic acid
(D) 1-phenyl-3-(p-chlorophenyl)-pyrazol-4-acetic acid
(E) 3,5-dimethyl-1-n-butyl-pyrazol-4-acetic acid
(F) 3,5-dimethyl-1-(p-methoxyphenyl)-pyrazol-4-acetic acid
(G) 3-methyl-1,5-diphenyl-pyrazol-4-acetic acid
(H) -methyl-1,3-triphenyl-pyrazol-4-acetic acid
(I) 1-phenyl-5-(p-chlorophenyl)-pyrazol-4-acetic acid
(K) 1-n-butyl-3,5-diphenyl-pyrazol-4-acetic acid
(L) 3,5-diphenyl-1-(p-chlorophenyl)-pyrazol-4-acetic acid
(M) 1-phenyl-3,5-bis-(p=chlorophenyl)-pyrazol-4-acetic acid
(N) 1-phenyl-3,5-bis-(m=methoxyphenyl)-pyrazol-4-acetic acid
(O) 3,5-diphenyl-1-(α,α,α-trifluoro-m-tolyl)pyrazol-4-acetic acid-ethyl ester
(P) 3,5-dimethyl-1-phenyl-pyrazol-4-acetamide
(Q) 3,5-dimethyl-1-phenyl-pyrazol-4-acetonitrile
(R) 1-phenyl-3-(p-methoxyphenyl)-pyrazol-4-acetonitrile The following Table I demonstrates the effectiveness of the pyrazol compounds of the general Formula In in retarding inflammation at the carrageenin edema of the rear paw of the rat (Winter, Risley and Nuss, Proc. Soc. exp. Biol. Med. 111 544, (1962) and at the ultraviolet erythema of the skin on the back of the guinea pig (Winder et al., Arch. Int. Pharmacodyn, 116, 261 (1958).

TABLE I

| | ANTIPHLOGISTIC EFFECT | | | | Toxicity $LD_{50}$ After a single dose in the mouse[3] i.p. mg/kg |
|---|---|---|---|---|---|
| | Retardation of the | | | | |
| | Carrageenin Edema | | UV-Erythema | | |
| Compound | by 40% mg/kg oral | by Relative Effect[4] | by 50% mg/kg oral | by Relative Effect[4] | |
| Phenylbutazon | 30 | 1.0 | 16 | 1.0 | 250 |
| Indomethacin | 4 | 7.5 | 20 | 0.8 | 45 |
| A | 5 | 6.0 | 3 | 5.3 | 312 |
| B | 10 | 3.0 | 1.5 | 10.7 | 370 |
| C | 20 | 1.5 | 2.5 | 6.4 | 1150 |
| D | 2.5 | 12.0 | 3 | 5.3 | 340 |
| E | 50 | 0.6 | — | — | 1400 |
| F | 50 | 0.6 | — | — | 1000 |
| G | — | — | 20 | 0.8 | 500 |
| H | 30 | 1.0 | 5 | 3.2 | 199 |

[3]Dose, at which 50% of the animals died within 72 hours after administration of the substance
[4]Phenylbutazon = 1.0

The following Table II demonstrates the analgesic effectiveness of the new pyrazol compounds of the general Formula I.

TABLE II

| | ANALGESIC EFFECT | | | | | | |
|---|---|---|---|---|---|---|---|
| Compound | $ED_{20}$ mg/kg oral | $ED_{20}$ Relative | $ED_{40}$ mg/kg oral | $ED_{40}$ Relative | $LD_5$ mg/kg I.P. | $LD_{50}$ mg/kg I.P. | Theurapeutic Index $LD_5/ED_{40}$ |
| Phenylbutazon | 150 | 0.3 | — | — | 185 | 250 | — |
| Aminophenazone | 50 | 1.0 | 140 | 1.0 | 270 | 330 | 1.9 |
| B | 10 | 5.0 | 50 | 2.8 | 190 | 373 | 3.8 |
| I | 50 | 1.0 | 70 | 2.0 | 180 | 279 | 2.6 |
| K | 20 | 2.5 | 80 | 1.8 | 360 | 430 | 4.5 |
| L | 15 | 3.3 | 55 | 2.5 | — | c.a.80 | — |
| M | 7 | 7.1 | 20 | 7.0 | 38 | 51 | 1.9 |
| N | 30 | 1.7 | 55 | 2.5 | 200 | 312 | 3.6 |
| O | 50 | 1.0 | 70 | 2.0 | — | — | — |
| P | 50 | 1.0 | 150 | 0.9 | 500 | 500 | 3.3 |
| Q | 20 | 2.5 | 40 | 3.5 | — | — | — |
| R | 50 | 1.0 | 80 | 1.8 | — | — | — |

The analgesic effect is measured as the mean delay in the defense reaction of the mouse by 20% ($ED_{20}$) and 40% ($ED_{40}$) during 2 hours upon thermal stimulation of the root of the tail by a heat beam relative to aminophenazone.

It is evident that typical compounds of the invention are effective analgesics over a wide dosage range as from 7 to about 50 mg/kg.

In addition thereto, the new pyrazole compounds of the invention effect a lowering of the temperature in mammalians: 60 mg/kg of compound A and 25 mg/kg of compound L, administered i.p. to the rat lower the normal temperature of the rat by 15° C. Both compounds are therefore more effective in this respect than aminophenazone, of which 70 mg/kg i.p. are required to achieve the same effect.

The compounds of the invention are well suited for the control and treatment of a variety of rheumatoid and other inflammatory disorders and illnesses in man, e.g. of acute and chronic polyarthritis, arthroses, rhumatic fever, sore postoperative swellings and inflammations, gout, effusions of the joint, musculoskeletal disorders, ankylosing spondylitis, thrombophlebitis, sprains, as well as of states of pain of various genesis, for instance neuritides, headache and spasms. Generally, the new compounds may be administered in per diem doses of 1 to 2000 mg., and especially of 20 to 500 mg.

The present invention concerns also new medicaments, which comprise a pharmaceutical carrier material and at least one of the new pyrazol-4-acetic acid compounds of the general Formula I or of at least one salt of such compound with a pharmacologically acceptable base. The new medicaments preferably contain also at least one of the conventional pharmacologically acceptable adjuvants. The invention concerns also new medicaments which contain as the therapeutically effective component at least one of the new compounds of the general Formula I or a salt thereof with a pharmacologically acceptable base in combination with at least one other therapeutically effective material.

The new medicament may be produced in conventional manner by mixing the compound or its salt with a pharmaceutical carrier material, such as a filler, a diluent, a corrigens and/or any other component useful in the compounding of medicaments.

The new medicaments of the invention are, depending on their composition and form, useful for oral, or rectal administration. The solution of the salt may also be used for parenteral administration, e.g. for intramuscular or intravenous administration.

For the oral administration, the therapeutically effective compound of the invention may be compounded in form of tablets, dragees, granulates, capsules, syrup or in form of drinkable solutions. For the protection of the therapeutically effective components, it is often of benefit, to provide the tablets with a coating, which is resistant against the gastric fluids, and especially against the gastric acid.

The tablets are preferably compounded with the conventional pharmaceutical carriers, such as lactose, saccharose, corn starch, potato starch, amylopectin, gelatine, ethyl cellulose, gum arabic, talc, polyethylene glycol. They may also contain the usual adjuvants such as magnesium stearate or calcium stearate.

For the rectal administration, the new medicaments may be compounded in the form of suppositories, and for parenteral application they are compounded in form of sterile solutions, preferably in the form of isotonic solutions.

In the following is provided an example of the composition of tablets in accordance with the invention.

Tablets:
Each tablet contains:
25 mg 1,3,5-triphenyl-pyrazol-4-acetic acid
63 mg corn starch
160 mg lactose
2 mg magnesium stearate The finely ground and sifted 1,3,5-triphenyl-pyrazol-4-acetic acid is mixed with the other components and the mixture is pressed to tablets.

Standard modes of application are applicable for the described compound, as is evident to one skilled in the art from the above. If further details regarding the above were needed, reference is made to *The Pharmaceutical Basis of Therapeutics*, 3rd Ed. *Goodman & Gilman*, especially pages 335-341, The Pyrazolon Derivatives.

In general for recrystallization of the pure product, the product obtained in the above-described procedure is dissolved in the first solvent, (for instance water, or ethyl acetate and precipitated from a non-solvent such as a lower alkanol, like ethanol or petroleum ether. Suitable range of these two solvent/non-solvent is about 1:5 to 5:1.

The adjustment of the pH is conveniently performed with a strong mineral acid, such as sulfuric acid, or hydrochloric acid with the addition of a lower alkanol, like methanol or acetic acid (glacial acetic acid) to promote dissolving.

We claim:

1. An anti-inflammatory, analgesic or antipyretic drug composition comprising a mixture of at least one pharmaceutically acceptable carrier and in an amount effective to provide anti-inflammatory, analgesic or antipyretic action, at least one of 1-phenyl-3,5-di(2-furyl) pyrazol-4-acetic acid or a salt of this compound with a pharmacologically acceptable base.

2. An anti-inflammatory, analgesic or antipyretic drug composition comprising a mixture of at least one pharmaceutically acceptable carrier and in an amount effective to provide anti-inflammatory, analgesic or antipyretic action, at least one of 1-phenyl-3-(p-fluorophenyl)-pyrazol-4-acetic acid or a salt of this compound with a pharmacologically acceptable base.

3. An anti-inflammatory, analgesic or antipyretic drug composition comprising a mixture of at least one pharmaceutically acceptable carrier and in an amount effective to provide anti-inflammatory, analgesic or antipyrectic action, at least one of 1-phenyl-3-(p-bromophenyl)-pyrazol-4-acetic acid or a salt of this compound with a pharmacologically acceptable base.

4. An anti-inflammatory, analgesic or antipyretic drug composition comprising a mixture of at least one pharmaceutically acceptable carrier and in an amount effective to provide anti-inflammatory, analgesic or antipyretic action, at least one of 1-phenyl-3-(2-naphthyl)-pyrazol-4-acetic acid or a salt of this compound with a pharmacologically acceptable base.

5. An anti-inflammatory, analgesic or antipyretic drug composition comprising a mixture of at least one pharmaceutically acceptable carrier and in an amount effective to provide anti-inflammatory, analgesic or antipyretic action, at least one of 1-phenyl-3-(p-chlorophenyl)-pyrazol-4-acetic acid or a salt of this compound with a pharmacologically acceptable base.

6. An anti-inflammatory, analgesic or antipyretic drug composition comprising a mixture of at least one pharmaceutically acceptable carrier and in an amount effective to provide anti-inflammatory, analgesic or antipyretic action, at least one of 1,3-diphenyl-pyrazol-4-acetic acid or a salt of this compound with a pharmacologically acceptable base.

7. An anti-inflammatory, analgesic or antipyretic drug composition comprising a mixture of at least one pharmaceutically acceptable carrier and in an amount effective to provide anti-inflammatory, analgesic or antipyretic action, at least one of 1-phenyl-3-p-tolyl-pyrazol-4-acetic acid or a salt of this compound with a pharmacologically acceptable base.

8. An anti-inflammatory, analgesic or antipyretic drug composition comprising a mixture of at least one pharmaceutically acceptable carrier and in an amount effective to provide anti-inflammatory, analgesic or antipyretic action, 1-(p-chlorophenyl)-3,5-diphenyl-4-pyrazol acetic acid.

9. An anti-inflammatory, analgesic or antipyretic drug composition comprising a mixture of at least one pharmaceutically acceptable carrier and in an amount effective to provide anti-inflammatory, analgesic or antipyretic action, at least one of the pharmaceutically acceptable salts of 1-(p-chlorophenyl)-3,5-diphenyl-4-pyrazol acetic acid.

10. An anti-inflammatory, analgesic or antipyretic drug composition comprising a mixture of at least one pharmaceutically acceptable carrier and in an amount effective to provide anti-inflammatory, analgesic or antipyretic action, 1-(p-bromophenyl)-3,5-diphenyl-4-pyrazol acetic acid.

11. An anti-inflammatory, analgesic or antipyretic drug composition comprising a mixture of at least one pharmaceutically acceptable carrier and in an amount effective to provide anti-inflammatory, analgesic or antipyretic action, at least one of the pharmaceutically acceptable salts of 1-(p-bromophenyl)-3,5-diphenyl-4-pyrazol acetic acid.

12. An anti-inflammatory, analgesic or antipyretic drug composition comprising a mixture of at least one pharmaceutically acceptable carrier and in an amount effective to provide anti-inflammatory, analgesic or antipyretic action, 1,3,5-triphenyl-4-pyrazol acetic acid or a salt of this compound with a pharmacologically acceptable base.

13. An anti-inflammatory, analgesic or antipyretic drug composition comprising a mixture of at least one pharmaceutically acceptable carrier and in an amount effective to provide anti-inflammatory, analgesic or antipyretic action, at least one compound having the formula

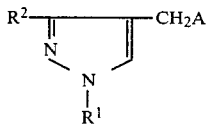

wherein $R^1$ and $R^2$ are selected from the group consisting of phenyl, halophenyl, lower alkylphenyl, dimethylphenyl, lower alkoxyphenyl, dimethoxyphenyl, lower alkylmercaptophenyl, trifluoromethylphenyl, furyl, thienyl and naphthyl with the proviso that at least one of $R^1$ and $R^2$ is phenyl or substituted phenyl and A is selected from the group consisting of —COOH, COOR$^5$, wherein $R^5$ is lower alkyl, and —CONH$_2$.

14. An anti-inflammatory, analgesic or antipyretic drug composition comprising a mixture of at least one pharmaceutically acceptable carrier and in an amount effective to provide anti-inflammatory, analgesic or antipyretic action, at least one compound of the formula

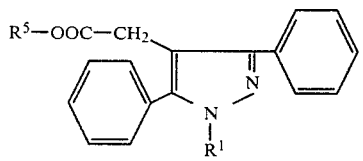

wherein $R^1$ is hydrogen, lower alkyl, phenyl, phenyl monosubstituted with lower alkyl, lower alkoxy or halogen, naphthyl, benzyl or benzyl wherein the phenyl ring is monosubstituted with lower alkoxy or halogen and $R^5$ is hydrogen or lower alkyl.

15. The drug composition of claim 14, wherein $R^5$ is hydrogen.

16. The drug composition of claim 14, wherein $R^5$ is lower alkyl.

17. The drug composition of claim 16, wherein said lower alkyl is methyl or ethyl.

18. An anti-inflammatory, analgesic or antipyretic drug composition comprising a mixture of at least one pharmaceutically acceptable carrier and in an amount effective to provide anti-inflammatory, analgesic or antipyretic action, methyl 1,3,5-triphenyl-4-pyrazol acetate.

19. An anti-inflammatory, analgesic or antipyretic drug composition comprising a mixture of at least one pharmaceutically acceptable carrier and in an amount effective to provide anti-inflammatory, analgesic or antipyretic action, the ethyl ester of 1,3,5-triphenyl-4-pyrazol acetic acid.

20. An anti-inflammatory, analgesic or antipyretic drug composition comprising a mixture of at least one pharmaceutically acceptable carrier and in an amount effective to provide anti-inflammatory, analgesic or antipyretic action, at least one pyrazol-4-acetic acid derivative of the formula

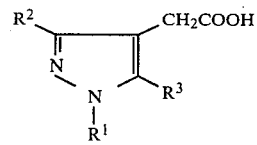

wherein $R^1$ is phenyl; $R^2$ is phenyl, p-halogenophenyl, p-methyl-phenyl or furyl; $R^3$ is hydrogen, phenyl, or furyl or a salt of said compound with a pharmacologically acceptable base.

21. The drug composition of claim 20, wherein $R^2$ is phenyl or p-halogenophenyl, and $R^3$ is hydrogen or phenyl.

22. The drug composition of claim 21, wherein $R^2$ is phenyl or p-halogenophenyl, and $R^3$ is hydrogen.

23. The drug composition of claim 22, wherein $R^2$ is p-halogenophenyl.

24. The drug composition of claim 23, wherein $R^2$ is p-bromophenyl.

25. The drug composition of claim 20, wherein the salt is a lithium, sodium, potassium, magnesium, calcium, ammonium, ethanolamine, diethanolamine, triethanolamine, ethylenediamine, glucosamine or N-methyl glucosamine salt.

26. An anti-inflammatory, analgesic or antipyretic drug composition comprising a mixture of at least one pharmaceutically acceptable carrier and in an amount effective to provide anti-inflammatory, analgesic or antipyretic action, at least one pyrazol-4-acetic acid derivative of the formula

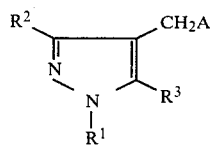

wherein $R^1$ is phenyl, $R^2$ is phenyl, p-halogenophenyl, p-methylphenyl, $R^3$ is hydrogen or phenyl and A is —COOH or —COOR$^5$ wherein $R^5$ is alkyl of 1 to 4 carbon atoms, or a salt of the acid with a pharmocologically acceptable base.

27. The drug composition of claim 26, wherein A is —COOH.

28. The drug composition of claim 26, wherein $R^1$, $R^2$ and $R^3$ are each one phenyl.

29. An anti-inflammatory, analgesic or antipyretic drug composition comprising a mixture of at least one pharmaceutically acceptable carrier and in an amount effective to provide anti-inflammatory, analgesic or antipyretic action, 1-phenyl-3-(p-chlorophenyl)-pyrazol-4-acetic acid methyl ester.

30. An anti-inflammatory, analgesic or antipyretic drug composition comprising a mixture of at least one pharmaceutically acceptable carrier and in an amount effective to provide anti-inflammatory, analgesic or antipyretic action, 1-phenyl-3,5,-bis-(m-methoxyphenyl)-pyrazol-4-acetic acid.

31. An anti-inflammatory, analgesic or antipyretic drug composition comprising a mixture of at least one pharmaceutically acceptable carrier and in an amount effective to provide anti-inflammatory, analgesic or antipyretic action, 1,3-diphenyl-5-(p-methoxyphenyl)-pyrazol-4-acetic acid.

32. An anti-inflammatory, analgesic or antipyretic drug composition comprising a mixture of at least one pharmaceutically acceptable carrier and in an amount effective to provide anti-inflammatory, analgesic or antipyretic action, 3,5-diphenyl-1-(p-chlorophenyl)-pyrazol-4-acetic acid.

33. An anti-inflammatory, analgesic or antipyretic drug composition comprising a mixture of at least one pharmaceutically acceptable carrier and in an amount effective to provide anti-inflammatory, analgesic or antipyretic action, 3,5-diphenyl-1-(o-chlorophenyl)-pyrazol-4-acetic acid.

34. An anti-inflammatory, analgesic or antipyretic drug composition comprising a mixture of at least one pharmaceutically acceptable carrier and in an amount effective to provide anti-inflammatory, analgesic or antipyretic action, 1-phenyl-3,5-bis-(p-chlorophenyl)-pyrazol-4-acetic acid.

35. An anti-inflammatory, analgesic or antipyretic drug composition comprising a mixture of at least one pharmaceutically acceptable carrier and in an amount effective to provide anti-inflammatory, analgesic or antipyretic action, 3,5-diphenyl-1-(m-chlorophenyl)-pyrazol-4-acetic acid.

36. A therapeutic method for treating a mammal suffering from symptoms of inflammation which comprises administering to the mammal an antiphlogistically effective amount of a pharmacologically acceptable dose of a composition according to any one of claims 5, 12, 13, 14, 15, 16, 20, 21, 22, 23, 25, 26, 27, 28 or 17.

37. A therapeutic method for treating a mammal suffering from symptoms of pain which comprises administering to the mammal an analgesically effective amount of a pharmacologically acceptable dose of a composition according to any one of claims 5, 12, 13, 14, 15, 16, 20, 21, 22, 23, 25, 26, 27, 28 or 17.

38. A therapeutic method for treating a mammal suffering from symptoms of fever which comprises administering to the mammal an antipyretically effective amount of a pharmacologically acceptable dose of a composition according to any one of claims 5, 12, 13, 14, 15, 16, 20, 21, 22, 23, 26, 27, 28 or 17.

39. The method of claim 36 wherein the effective amount is from 2.5 to 50 mg/Kg.

40. The method of claim 37 wherein the effective amount is from 7 to 50 mg/Kg.

41. The method of claim 38 wherein the effective amount is from 25 to 60 mg/Kg.

* * * * *